(12) United States Patent
Serhan et al.

(10) Patent No.: US 7,909,826 B2
(45) Date of Patent: Mar. 22, 2011

(54) LOW PROFILE SPINAL TETHERING METHODS

(75) Inventors: Hassan A. Serhan, S. Easton, MA (US);
Michael A. Slivka, Taunton, MA (US);
Mathew Hannen, Boston, MA (US);
Peter Newton, San Diego, CA (US);
Michael Nilsson, Cleveland Heights, OH (US)

(73) Assignee: DePuy Spine, Inc., Raynham, MA (US)

( * ) Notice: Subject to any disclaimer, the term of this patent is extended or adjusted under 35 U.S.C. 154(b) by 607 days.

(21) Appl. No.: 10/907,232

(22) Filed: Mar. 24, 2005

(65) Prior Publication Data

US 2006/0217714 A1    Sep. 28, 2006

(51) Int. Cl.
*A61B 17/84* (2006.01)

(52) U.S. Cl. ......................................................... 606/75

(58) Field of Classification Search .............. 606/60–61, 606/72–75, 219–221, 232, 246, 254, 255
See application file for complete search history.

(56) References Cited

U.S. PATENT DOCUMENTS

| 4,041,939 | A | | 8/1977 | Hall | |
|---|---|---|---|---|---|
| 4,047,523 | A | | 9/1977 | Hall | |
| 4,047,524 | A | | 9/1977 | Hall | |
| 4,050,464 | A | | 9/1977 | Hall | |
| 4,763,644 | A | | 8/1988 | Webb | |
| 5,154,719 | A | * | 10/1992 | Cotrel | 606/308 |
| 5,209,756 | A | * | 5/1993 | Seedhom et al. | 606/151 |
| 5,282,863 | A | * | 2/1994 | Burton | 606/61 |
| 5,352,229 | A | * | 10/1994 | Goble et al. | 606/72 |
| 5,385,583 | A | | 1/1995 | Cotrel et al. | |
| 5,487,742 | A | * | 1/1996 | Cotrel | 606/252 |
| 5,549,608 | A | | 8/1996 | Errico et al. | |
| 5,690,629 | A | * | 11/1997 | Asher et al. | 606/61 |
| 5,728,127 | A | | 3/1998 | Asher et al. | |
| 5,766,254 | A | * | 6/1998 | Gelbard | 623/17.16 |
| 5,782,831 | A | | 7/1998 | Sherman et al. | |
| 5,863,293 | A | | 1/1999 | Richelsoph | |
| 5,888,221 | A | * | 3/1999 | Gelbard | 623/17.11 |
| 5,899,905 | A | | 5/1999 | Errico et al. | |
| 5,925,047 | A | | 7/1999 | Errico et al. | |

(Continued)

FOREIGN PATENT DOCUMENTS

EP    1 060 709    12/2000

(Continued)

OTHER PUBLICATIONS

Oct. 5, 2007, Office Action for U.S. Appl. No. 10/907,231.

(Continued)

*Primary Examiner* — Eduardo C Robert
*Assistant Examiner* — Elana B Fisher
(74) *Attorney, Agent, or Firm* — Nutter McClennen & Fish LLP

(57) ABSTRACT

Methods and devices for treating spinal deformities are provided. In one exemplary embodiment, a low-profile spinal anchoring device is provided for receiving a spinal fixation element, such as a tether, therethrough. The device generally includes a staple body that is adapted to seat a spinal fixation element, a fastening element for fixing the staple body to bone, and a locking assembly for coupling a spinal fixation element to the staple body. In one embodiment, the locking assembly includes a washer that is adapted to couple to the staple body such that the spinal fixation is disposed therebetween, and a locking nut that is adapted to engage the staple body to mate the washer to the staple body.

23 Claims, 26 Drawing Sheets

U.S. PATENT DOCUMENTS

| | | | |
|---|---|---|---|
| 5,947,969 | A | 9/1999 | Errico et al. |
| 5,951,553 | A | 9/1999 | Betz |
| 5,984,928 | A * | 11/1999 | Hermann ............... 606/324 |
| 6,077,262 | A * | 6/2000 | Schlapfer et al. ........... 606/61 |
| 6,136,002 | A * | 10/2000 | Shih et al. ................ 606/250 |
| 6,248,106 | B1 | 6/2001 | Ferree |
| 6,264,658 | B1 | 7/2001 | Lee et al. |
| 6,287,308 | B1 | 9/2001 | Betz |
| 6,296,643 | B1 | 10/2001 | Hopf |
| 6,299,613 | B1 | 10/2001 | Ogilvie |
| 6,325,805 | B1 | 12/2001 | Ogilvie |
| 6,423,065 | B2 | 7/2002 | Ferree |
| 6,436,099 | B1 | 8/2002 | Drewry et al. |
| 6,464,706 | B1 | 10/2002 | Winters |
| 6,488,683 | B2 | 12/2002 | Lieberman |
| 6,524,311 | B2 * | 2/2003 | Gaines, Jr. .............. 606/278 |
| 6,542,311 | B2 | 4/2003 | Nagahara |
| 6,551,320 | B2 | 4/2003 | Lieberman |
| 6,551,322 | B1 * | 4/2003 | Lieberman ............... 606/246 |
| 6,616,669 | B2 | 9/2003 | Ogilvie |
| 6,623,484 | B2 | 9/2003 | Betz |
| 6,746,450 | B1 | 6/2004 | Wall et al. |
| 6,773,437 | B2 | 8/2004 | Ogilvie et al. |
| 6,783,527 | B2 | 8/2004 | Drewry et al. |
| 7,367,978 | B2 | 5/2008 | Drewry et al. |
| 2001/0010000 | A1 | 7/2001 | Gertzbein et al. |
| 2001/0027319 | A1 | 10/2001 | Ferree |
| 2001/0029375 | A1 | 10/2001 | Betz et al. |
| 2002/0007184 | A1 | 1/2002 | Ogilvie et al. |
| 2002/0019636 | A1 * | 2/2002 | Ogilvie et al. ............ 606/75 |
| 2002/0042615 | A1 * | 4/2002 | Graf et al. ............... 606/73 |
| 2002/0055739 | A1 | 5/2002 | Lieberman |
| 2002/0055740 | A1 * | 5/2002 | Lieberman ............... 606/61 |
| 2002/1005574 | * | 5/2002 | Lieberman ............... 606/61 |
| 2002/0143329 | A1 | 10/2002 | Serhan et al. |
| 2002/0193795 | A1 | 12/2002 | Gertzbein et al. |
| 2002/0198526 | A1 | 12/2002 | Shaolian et al. |
| 2003/0023241 | A1 | 1/2003 | Drewry et al. |
| 2003/0083657 | A1 | 5/2003 | Drewry |
| 2003/0088251 | A1 | 5/2003 | Braun et al. |
| 2003/0191470 | A1 * | 10/2003 | Ritland .................. 606/61 |
| 2004/0034351 | A1 | 2/2004 | Sherman et al. |
| 2004/0073222 | A1 * | 4/2004 | Koseki ................. 606/75 |
| 2004/0138660 | A1 | 7/2004 | Serhan |
| 2004/0138666 | A1 | 7/2004 | Molz et al. |
| 2004/0153068 | A1 * | 8/2004 | Janowski et al. ............ 606/61 |
| 2004/0172025 | A1 | 9/2004 | Drewry |
| 2004/0236327 | A1 | 11/2004 | Paul et al. |
| 2004/0260284 | A1 | 12/2004 | Parker |
| 2006/0217713 | A1 | 9/2006 | Serhan et al. |
| 2006/0217714 | A1 | 9/2006 | Serhan et al. |
| 2006/0217715 | A1 | 9/2006 | Serhan et al. |
| 2008/0065114 | A1 | 3/2008 | Stone et al. |
| 2008/0140122 | A1 | 6/2008 | Bethell |
| 2008/0140123 | A1 | 6/2008 | Ferree |
| 2008/0140133 | A1 | 6/2008 | Allard et al. |
| 2008/0161854 | A1 | 7/2008 | Bae et al. |
| 2008/0234679 | A1 | 9/2008 | Sarin et al. |
| 2008/0262546 | A1 | 10/2008 | Calvosa et al. |
| 2008/0262550 | A1 | 10/2008 | Ferree |
| 2008/0294198 | A1 | 11/2008 | Jackson |
| 2008/0300599 | A1 | 12/2008 | Anapliotis et al. |
| 2008/0312695 | A1 | 12/2008 | Sybert et al. |
| 2008/0319487 | A1 | 12/2008 | Fielding et al. |
| 2009/0018662 | A1 | 1/2009 | Pasquet et al. |
| 2009/0054902 | A1 | 2/2009 | Mickiewicz et al. |

FOREIGN PATENT DOCUMENTS

| | | |
|---|---|---|
| GB | 1 519 139 | 7/1978 |
| GB | 1 551 704 | 8/1979 |
| GB | 1 551 705 | 8/1979 |
| GB | 1 551 706 | 8/1979 |
| GB | 1 551 707 | 8/1979 |
| GB | 2 173 104 | 10/1986 |
| WO | WO-00/64363 | 11/2000 |
| WO | WO-00/64364 | 11/2000 |
| WO | WO-00/64365 | 11/2000 |
| WO | WO-01/03570 A2 | 1/2001 |
| WO | WO-02/078574 | 10/2002 |
| WO | WO-03/003901 | 1/2003 |
| WO | WO-03/003902 | 1/2003 |
| WO | WO 03/037216 | 5/2003 |
| WO | WO-03/039330 | 5/2003 |
| WO | WO-2004/016186 | 2/2004 |
| WO | 2007060534 A2 | 5/2007 |

OTHER PUBLICATIONS

Response to Office Action filed Nov. 19, 2007 for U.S. Appl. No. 10/907,231.
Feb. 29, 2008, Office Action for U.S. Appl. No. 10/907,231.
Response to Office Action filed May 1, 2008 for U.S. Appl. No. 10/907,231.
Aug. 20, 2008, Final Office Action for U.S. Appl. No. 10/907,231.
Oct. 17, 2007, Office Action for U.S. Appl. No. 10/907,232.
Response to Office Action filed Dec. 12, 2007 for U.S. Appl. No. 10/907,232.
Mar. 18, 2008, Office Action for U.S. Appl. No. 10/907,232.
Response to Office Action filed May 1, 2008.
Aug. 8, 2008, Final Office Action for U.S. Appl. No. 10/907,232.
Oct. 25, 2007, Office Action for U.S. Appl. No. 10/907,233.
Response to Office Action filed Dec. 12, 2007 for U.S. Appl. No. 10/907,233.
Mar. 18, 2008, Final Office Action for U.S. Appl. No. 10/907,233.
Response to Final Office Action filed May 1, 2008 for U.S. Appl. No. 10/907,233.
May 15, 2008, Advisory Action for U.S. Appl. No. 10/907,233.
Remarks with Request for Continued Examination filed Jun. 16, 2008 for U.S. Appl. No. 10/907,233.
Jul. 10, 2008, Office Action (1st after RCE) for U.S. Appl. No. 10/907,233.
Nov. 13, 2008, Office Action for U.S. Appl. No. 10/907,231.
Jul. 10, 2008, Office Action for U.S. Appl. No. 10/907,233.
Dec. 24, 2008, Final Office Action for U.S. Appl. No. 10/907,233.
Oct. 30, 2008, Office Action for U.S. Appl. No. 10/907,232.
Dec. 24, 2008, Office Action for U.S. Appl. No. 10/907,233.
European Supplementary Search Report for EP06719044.7, dated Mar. 6, 2009. (6 pages).
J Bone Joint Surg Br Dwyer and Schafer 56-B (2): 218-224, 1994.
A.F. Dwyer, Experience of Anterior Correction of Scoliosis, Jun. 1973;(93):191-206.
Australian Office Action for 2006229616, dated Jul. 13, 2009. (5 pages).
Mexican Office for MX/A/2007/011782, dated Mar. 25, 2010. (4 pages).
Reponse to Office Action filed May 1, 2008 for U.S. Appl. No. 10/907,232.

* cited by examiner

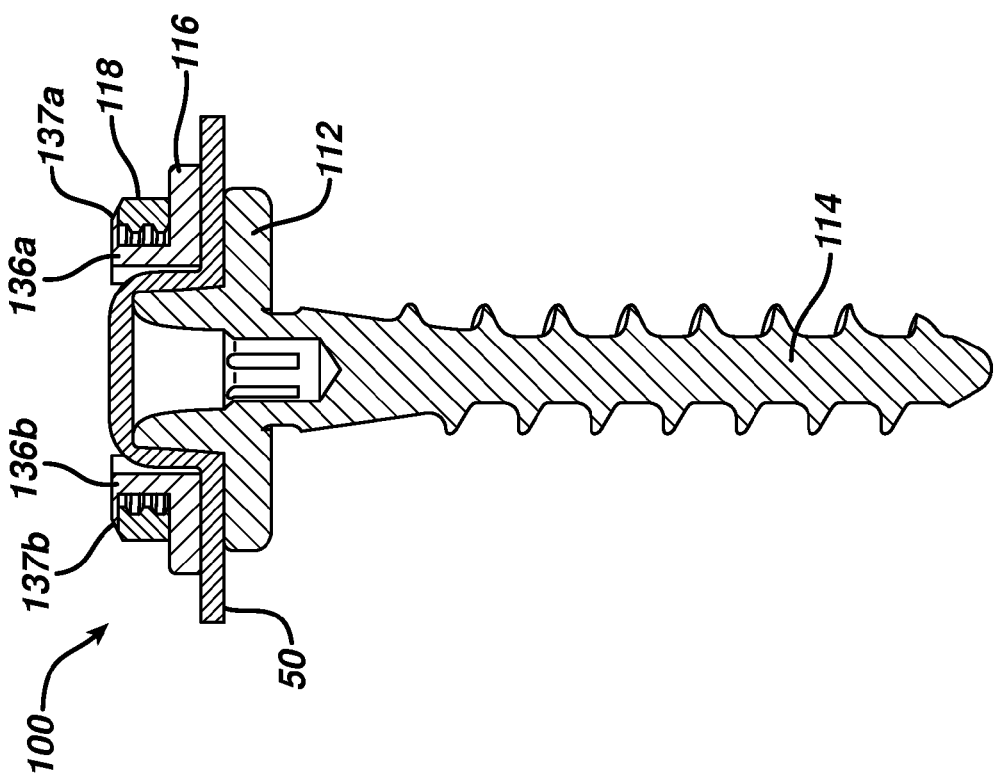
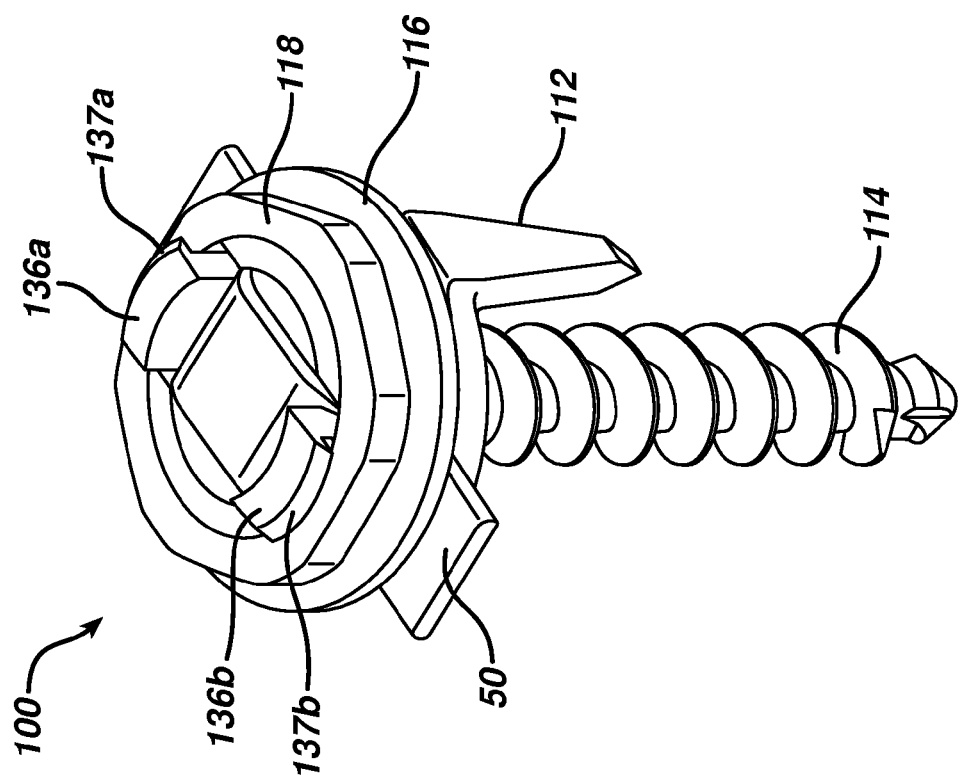

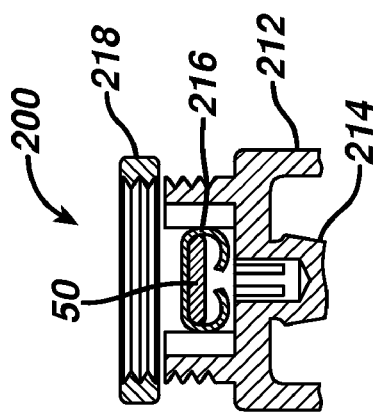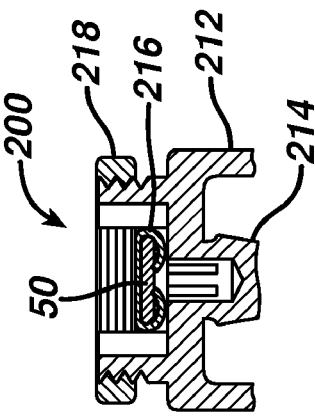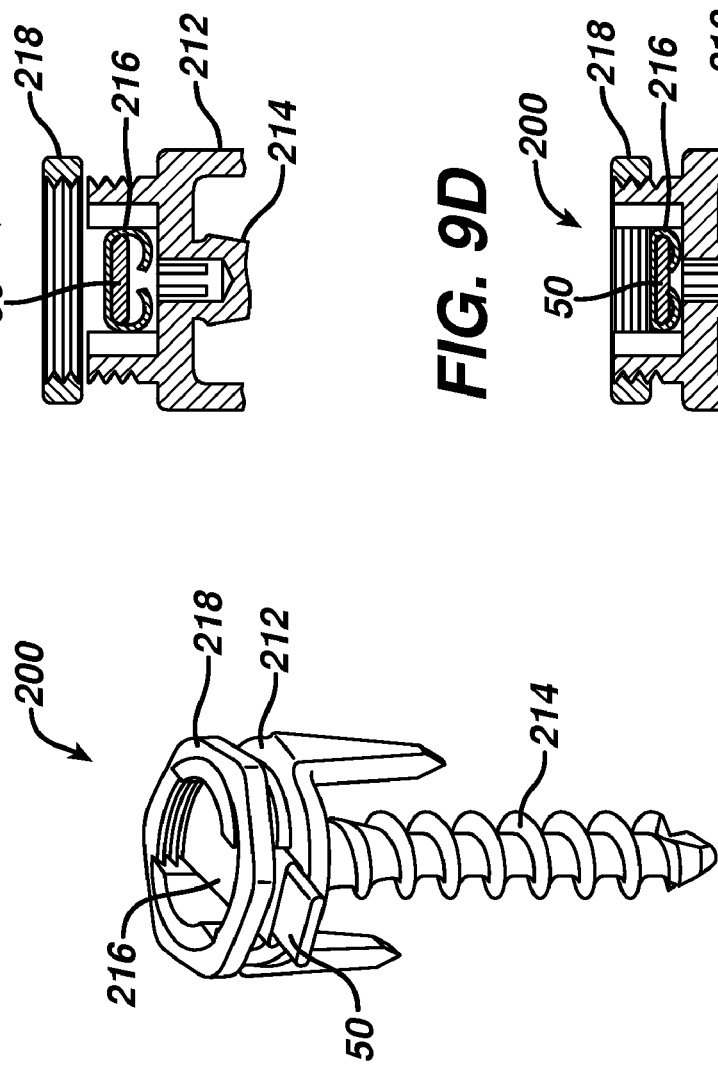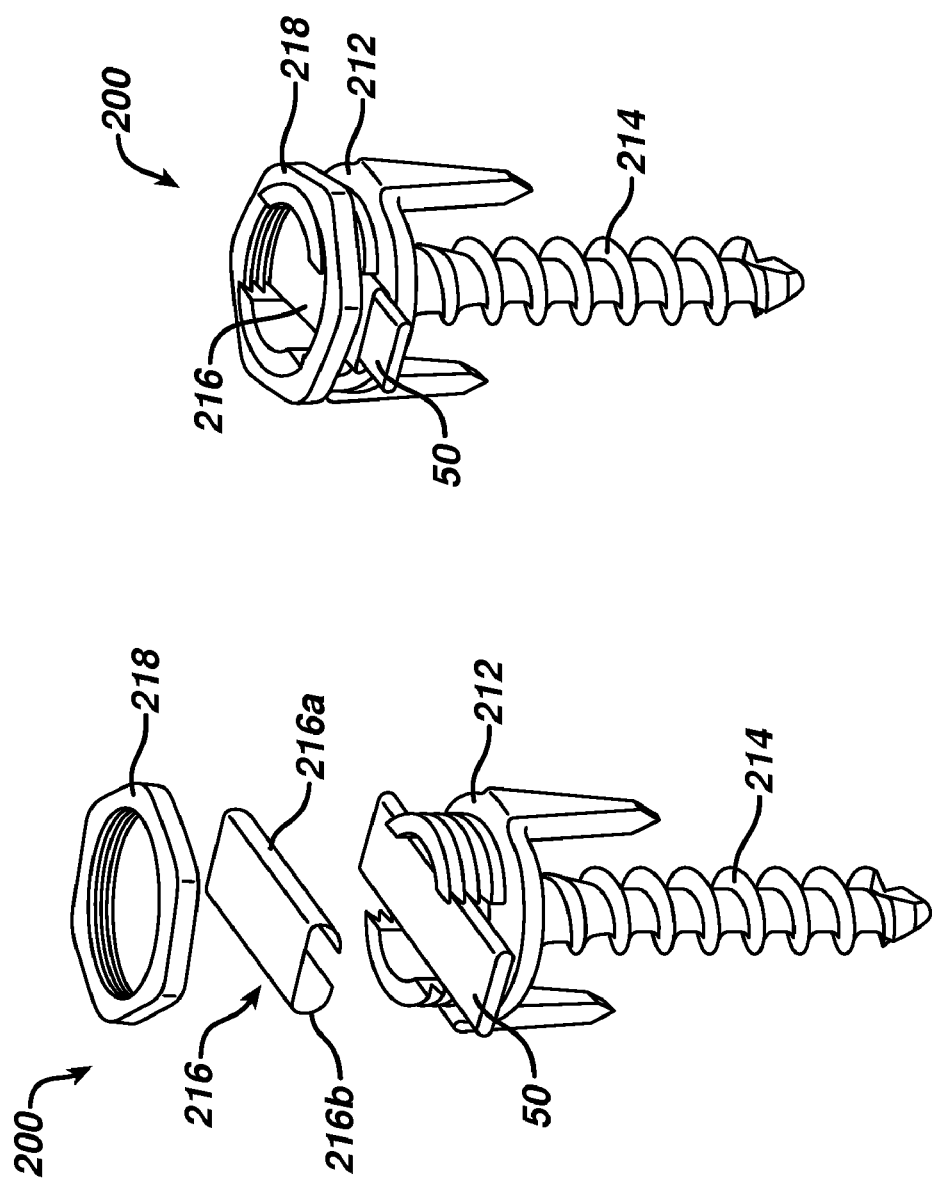

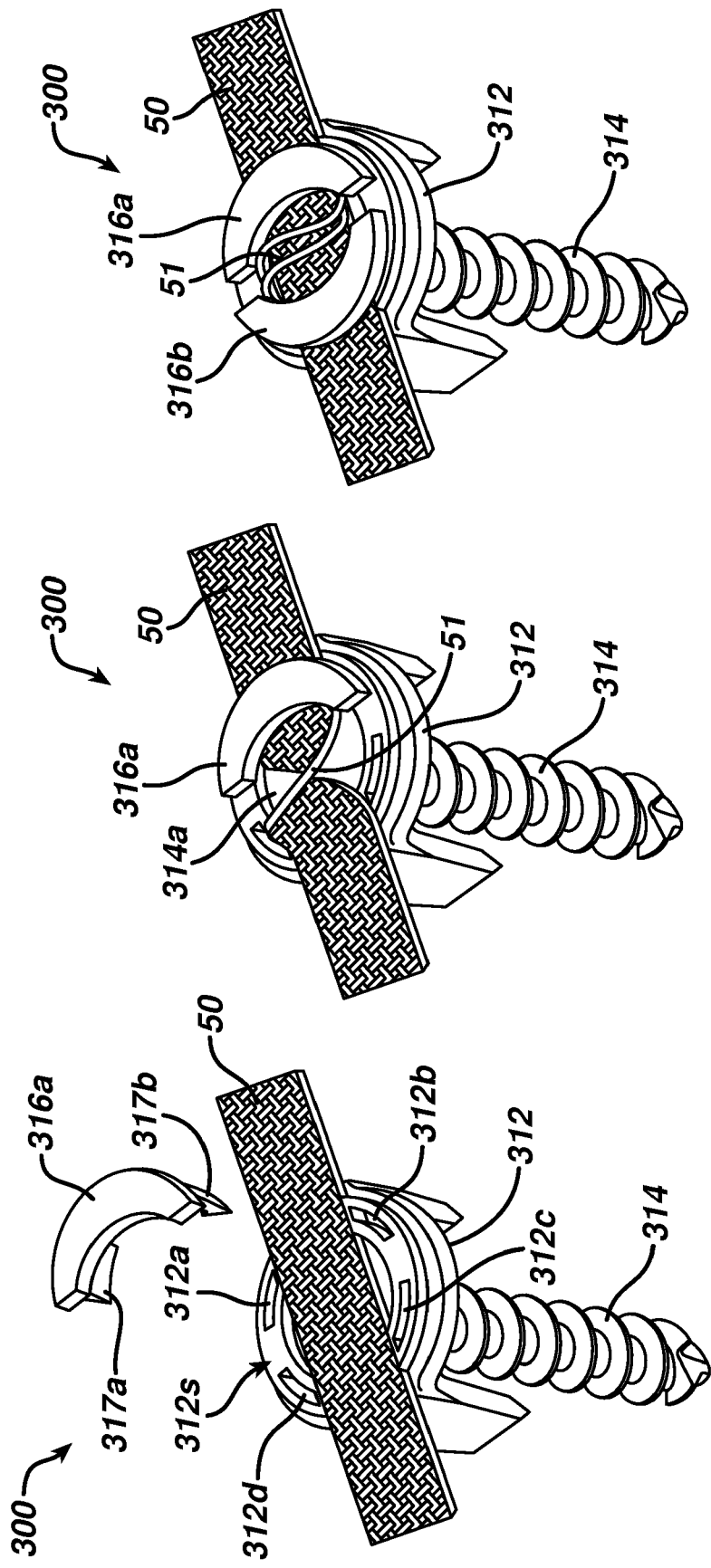

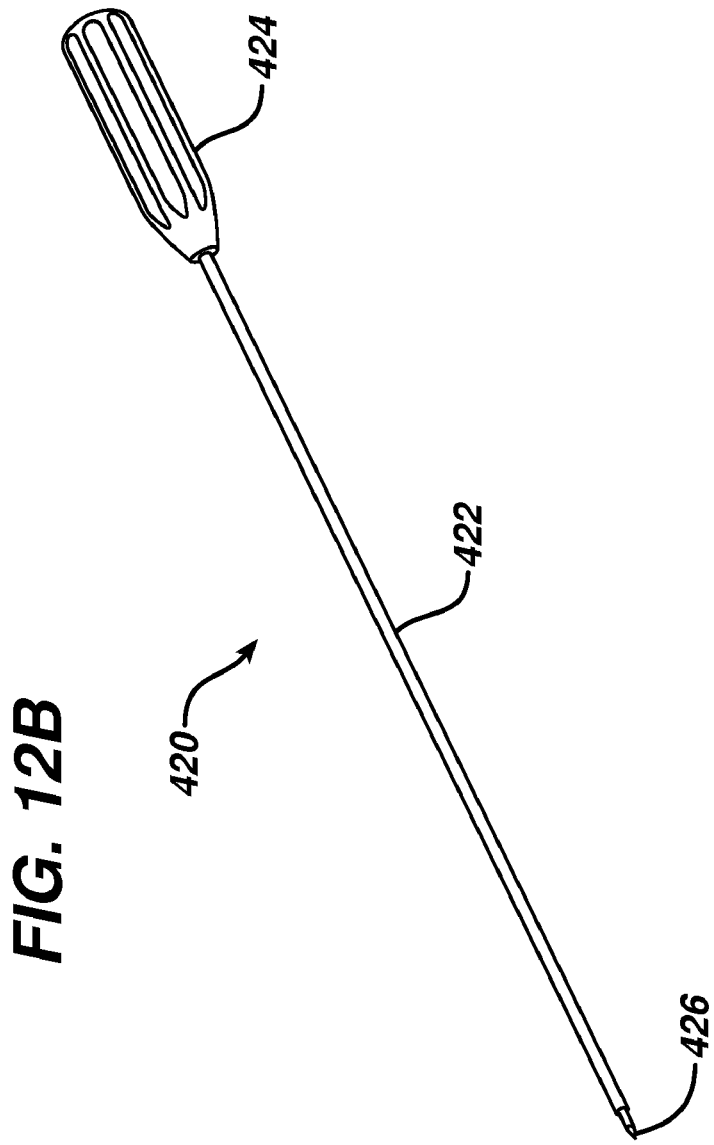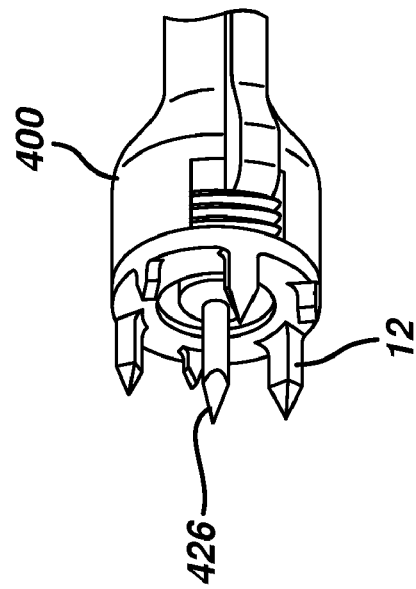

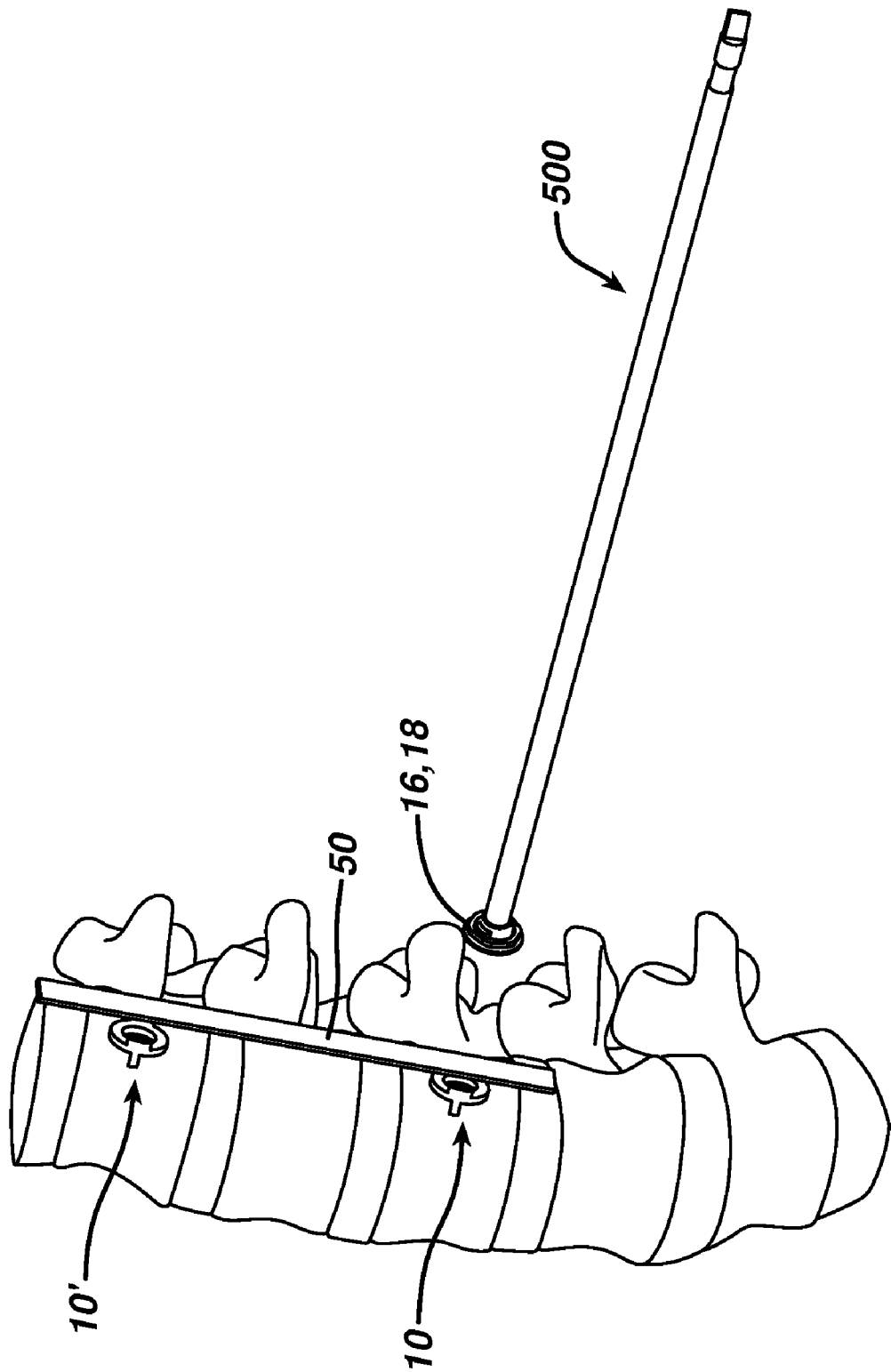

LOW PROFILE SPINAL TETHERING METHODS

BACKGROUND

Spinal deformities, which include rotation, angulation, and/or curvature of the spine, can result from various disorders, including, for example, scoliosis (abnormal curvature in the coronal plane of the spine), kyphosis (backward curvature of the spine), and spondylolisthesis (forward displacement of a lumbar vertebra). Early techniques for correcting such deformities utilized external devices that apply force to the spine in an attempt to reposition the vertebrae. These devices, however, resulted in severe restriction and in some cases immobility of the patient. Furthermore, current external braces have limited ability to correct the deformed spine and typically only prevent progression of the deformity. Thus, to avoid this need, several rod-based techniques were developed to span across multiple vertebrae and force the vertebrae into a desired orientation.

In rod-based techniques, one or more rods are attached to the vertebrae at several fixation sites to progressively correct the spinal deformity. The rods are typically pre-curved intraoperatively to a desired adjusted spinal curvature. Wires as well as bone screws can be used to pull individual vertebra toward the rod. Once the spine has been substantially corrected, the procedure typically requires fusion of the instrumented spinal segments.

While several different rod-based systems have been developed, they tend to be cumbersome, requiring complicated surgical procedures with long operating times to achieve correction. Further, intraoperative adjustment of rod-based systems can be difficult and may result in loss of mechanical properties due to multiple bending operations. The rigidity and permanence of rigid rod-based systems can also hinder or prevent growth of the spine and they generally require fusion of many spine levels, drastically reducing the flexibility of the spine. In addition to excessive rigidity, other drawbacks with current devices include dislodgement and a high profile.

Accordingly, there remains a need for improved methods and devices for correcting spinal deformities and, in particular, there remains a need for low-profile, flexible non-fusion spinal correction methods and devices.

BRIEF SUMMARY

The present invention provides methods and devices for treating spinal deformities. In one exemplary embodiment, a spinal anchoring device is provided and it includes a staple body, a fastening element, and a locking assembly. The staple body can be adapted to receive the fastening element for mating the staple body to bone, and to seat a tether. The locking assembly can be applied to the staple body to engage the tether and substantially prevent movement thereof relative to the device.

While the staple body can have a variety of configurations, in one embodiment the staple body includes a central opening formed therethrough and a pathway extending across the central opening for seating a tether. In an exemplary embodiment, the central opening includes a substantially spherical surface formed therearound for seating a complementary spherical surface formed on the fastening element. The staple body can also include opposed arms extending from opposed sides of a superior surface. The opposed arms can define the pathway therebetween. The configuration of the pathway can vary, but in one exemplary embodiment the pathway is non-linear, and more preferably it is tortuous. In another embodiment, the opposed arms can include threads formed on an external surface thereof for mating with corresponding threads formed on the locking assembly.

The fastening element can also have a variety of configurations, but in one embodiment the fastening element is adapted to extend through a central opening formed in the staple body to mate the staple body to bone. By way of non-limiting example, the fastening element can be a bone screw having a head and a shank. In an exemplary embodiment, the head of the bone screw includes a flange formed just distal to a proximal end of the shank of the bone screw and having a diameter that is greater than a diameter of the central opening formed in the staple body. The flange can also include a substantially spherical inferior surface that is adapted to correspond to a substantially spherical surface formed around the central opening of the staple body. The head of the bone screw can also include a proximal extension that is adapted to extend into the pathway of the staple body. The proximal extension can include a recess formed therein for receiving a tool adapted to drive the bone screw into bone.

The locking assembly can also have a variety of configurations, but in one embodiment it is adapted to engage the staple body such that a tether extending through the pathway extends between the locking assembly and the staple body. In an exemplary embodiment, the locking assembly includes a washer that is adapted to couple to the staple body such that a tether extending through the pathway is positioned between the washer and the staple body, and a locking nut that is adapted to engage the staple body to lock the washer to the staple body. While the shape of the washer can vary, one exemplary washer includes opposed openings formed therethrough for receiving the opposed arms on the staple body. The washer can also include a strut extending thereacross and adapted to be positioned between the opposed arms. In other exemplary embodiments, the locking assembly can be a nut, such as a set screw, or a washer that is separate from the staple body, or that is coupled to the staple body and movable between an open position and a closed position.

In yet another embodiment, the spinal anchoring device can include a deformable clip that is adapted to be disposed around a tether and positioned within the pathway such that the locking assembly is adapted to deform the clip to engage the tether when the locking assembly is mated to the staple body.

In other embodiments, the staple, the fastening element, and/or the locking assembly can include a tether-engaging feature formed thereon. In one exemplary embodiment, the tether-engaging features can be at least one groove formed on the superior surface of the staple and positioned in the pathway, and at least one complementary ridge formed on the locking assembly such that the at least one ridge and at least one groove are adapted to engage a tether seated in the pathway. In another embodiment, the tether-engaging feature can be a head formed on a proximal end of the fastening element and adapted to extend into the pathway such that the head alters a path of a tether seated in the pathway. In yet another embodiment, the tether-engaging feature can be a protrusion formed on an inferior surface of the locking assembly such that the protrusion is adapted to extend into a tether seated in the pathway.

An exemplary tether for use with a spinal anchoring device is also provided and it is in the form of a substantially flat elongate member having a cross-sectional width that is at least two times greater than a cross-sectional height. In an exemplary embodiment, the tether is formed from a biocompatible polymeric braided material, such as an ultra-high molecular weight polyethylene, or poly(ethylene terephthalate). In other embodiments, the tether can be formed from a bioabsorble material, such as poly(L-lactic acid).

An exemplary spinal anchoring system is also provided, which includes a substantially flat elongate tether, and an anchoring device that is adapted to mate to bone and that includes a pathway formed therethrough for seating the substantially flat elongate tether such that the tether is maintained in a substantially fixed position. In an exemplary embodiment, the anchoring device includes a staple that is adapted to penetrate bone and defining the pathway, a fastening element that is adapted to mate the staple to bone, and a locking assembly that is adapted to engage the staple to maintain the tether in a substantially fixed position between the locking assembly and the staple.

In certain aspects, the anchoring device can include at least one tether-engaging feature that is adapted to extend into the pathway to maintain the tether in a substantially fixed position. The tether-engaging feature can be, for example, a clip that is adapted to be disposed around the tether. In other embodiments, the tether-engaging feature can be a ridge formed on an inferior surface of the washer for extending into at least one corresponding complementary groove formed in a superior surface of the staple. The ridge(s) and the groove(s) can be adapted to engage the tether therebetween.

Various tools for implanting spinal anchoring devices are also provided. In one exemplary embodiment, a tool is provided having an elongate shaft with proximal and distal ends and an inner lumen extending therebetween. The distal end can include opposed deflectable members separated by an elongate slot, and the opposed deflectable members can include a substantially cylindrical portion having a recess formed in a distal surface thereof. In an exemplary embodiment, the recess is substantially rectangular, and it extends between the opposed deflectable members such that it separates a distal-most portion of the opposed deflectable members.

In another embodiment, an inserter system is provided having a fastener inserter tool with an elongate shaft having a substantially cylindrical member formed on the distal end thereof and including opposed arms, and a wrench having a hollow elongate shaft that is adapted to be slidably disposed over the fastener inserter tool, and having a distal end with a socket member formed thereon and adapted to receive a locking element. In one embodiment, the socket member of the wrench includes a hexagonal socket formed therein.

Methods for correcting spinal deformities are also provided, and in one exemplary embodiment the method includes implanting an anchoring element in bone, positioning a substantially flat elongate tether through the anchoring element, and applying a locking element to the anchoring element to engage the tether. In one embodiment, the anchoring element can be implanted in bone by impacting a staple into bone, and inserting a fastening element through the staple and into a bone hole to mate the staple to bone. In another embodiment, the anchoring element can be implanted in bone by inserting the fastening element into a bone hole to drive a staple into bone. In yet another embodiment, a locking element can be applied to the anchoring element by positioning a washer around opposed arms of staple of the anchoring element such that the tether is positioned between the washer and the staple. A locking nut can then be mated to the opposed arms.

In another exemplary embodiment, there is provided a method for correcting spinal deformities, which includes impacting at least one bone-penetrating member formed on an inferior surface of a staple body into a vertebra, inserting a fastening element through the staple body and into the vertebrae to attach the staple to the vertebra, positioning a tether on a superior surface of the staple such that the tether extends over a head of the fastening element, and applying a locking mechanism to the staple to maintain the tether in a substantially fixed position relative to the staple.

BRIEF DESCRIPTION OF THE DRAWINGS

The invention will be more fully understood from the following detailed description taken in conjunction with the accompanying drawings, in which:

FIG. 7A is a perspective view of another exemplary embodiment of a spinal anchoring device having a tether coupled thereto by a locking mechanism;

FIG. 7B is a cross-sectional view of the spinal anchoring device shown in FIG. 7A;

FIG. 9A is a perspective, disassembled view of another exemplary embodiment of a spinal anchoring device having a clip for engaging a tether extending therethrough;

FIG. 9B is a perspective, assembled view of the spinal anchoring device shown in FIG. 9A having the tether extending therethrough;

FIG. 9C is a cross-sectional view of a portion of the spinal anchoring device shown in FIG. 9A with the locking mechanism about to be coupled thereto;

FIG. 9D is a cross-sectional view of a portion of the spinal anchoring device shown in FIG. 9C with the locking mechanism coupled thereto;

FIG. 10A is a perspective, disassembled view of yet another exemplary embodiment of a spinal anchoring device having a tether extending therethrough and having a two-piece locking element;

FIG. 10B is a perspective, partially assembled view of the spinal anchoring device shown in FIG. 10A having the tether extending therethrough with a twist formed therein;

FIG. 10C is a perspective, fully assembled view of the spinal anchoring device shown in FIG. 10B having the tether extending therethrough;

FIG. 12B is a perspective view of the awl shown in FIG. 12A;

FIG. 12C is a perspective view of a distal end of the awl shown in FIG. 12B inserter through the staple inserter tool and staple shown in FIG. 12A;

FIG. 16A is an illustration showing a tether positioned relative to the two spinal anchoring devices implanted in the vertebrae shown in FIG. 15, and showing a fastener inserter tool about to apply a fastening element to one of the spinal anchoring devices;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In one exemplary embodiment, a low-profile spinal anchoring device is provided for receiving a spinal fixation element, such as a tether, therethrough. In use, several spinal anchoring devices can be implanted in several adjacent vertebrae, and the tether can be coupled to the spinal anchoring devices to halt growth of the spine on the side where the tether is applied. By halting the growth of the spine on the convex side of the deformity, subsequent growth of the spine on the concave side will cause the deformity to self-correct, thus gradually providing the correction while allowing the patient's overall height to increase. The methods and devices can, however, be used in a variety of other spinal applications. By way of non-limiting example, the spinal anchoring devices and/or tethers disclosed herein can be used for intra-operative deformity correction with subsequent fusion, as taught by Dr. A. F. Dwyer in the 1960's and 70's (Clin Orthop Rel Res 93, pp. 191-206, 1973, and J Bone Joint Surg 56B, pp. 218-224). In addition, they can be used for posterior dynamization to function as a decompressive device for stenosis and/or an adjunct to an intervertebral disc to unload the facets of the vertebra. A variety of exemplary methods and tools for implanting a spinal anchoring device are also provided.

Figure 1A:
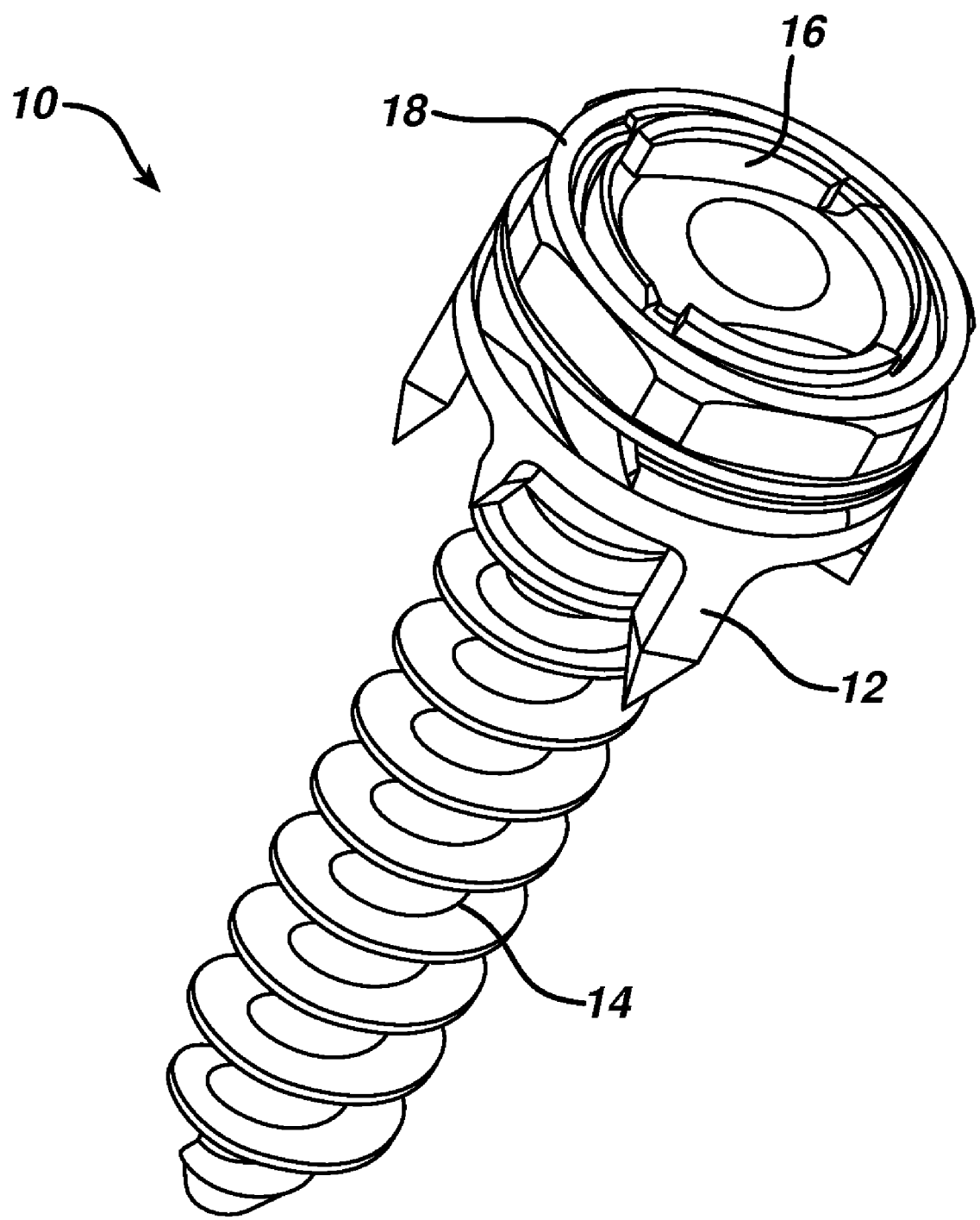
FIG. 1A is a perspective view of one exemplary embodiment of a spinal anchoring device.
Figure 1B:
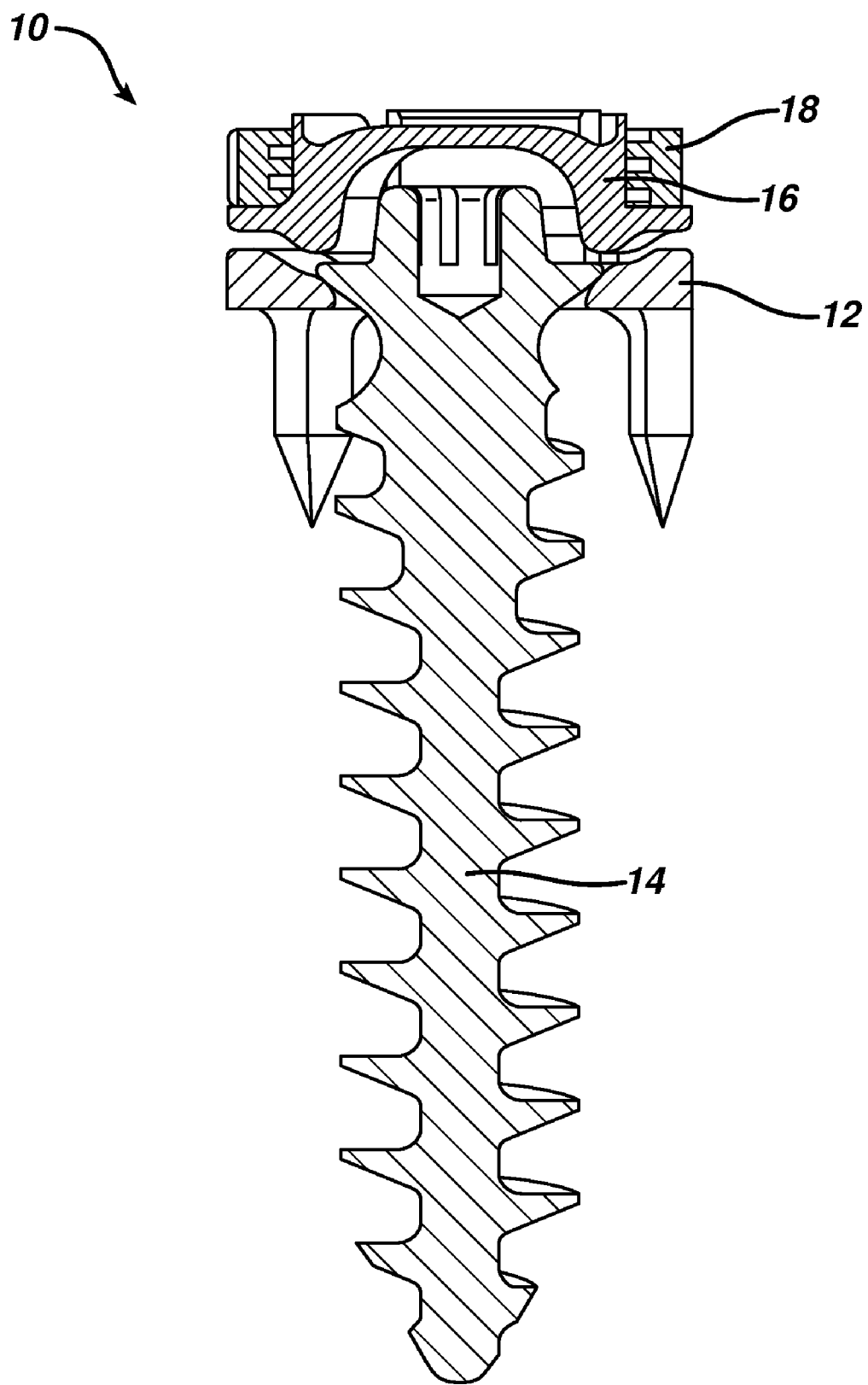
FIG. 1B is a cross-sectional view of the spinal anchoring device shown in FIG. 1A.

FIGS. 1A and 1B illustrate one exemplary embodiment of a spinal anchoring device 10. As shown, the device 10 generally includes a staple body 12 that is adapted to seat a spinal fixation element, a fastening element 14 for fixing the staple body 12 to bone, and a locking assembly for coupling a spinal fixation element to the staple body 12. In the illustrated exemplary embodiment, the locking assembly includes a washer 16 that is adapted to couple to the staple body 12 such that the spinal fixation element is disposed therebetween, and a locking nut 18 that is adapted to engage the staple body 12 to mate the washer 16 to the staple body 12. The locking assembly can, however, have a variety of other configurations and it can be separate from the staple body or coupled to the staple body.

Figure 2A:
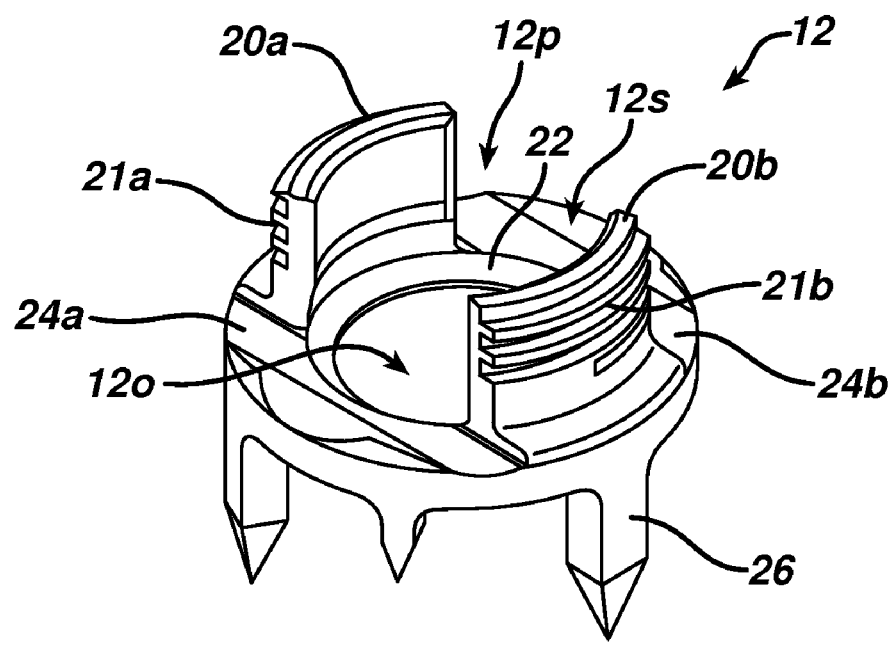
FIG. 2A is a top perspective view of a staple body of the spinal anchoring device shown in FIG. 1A.
Figure 2B:
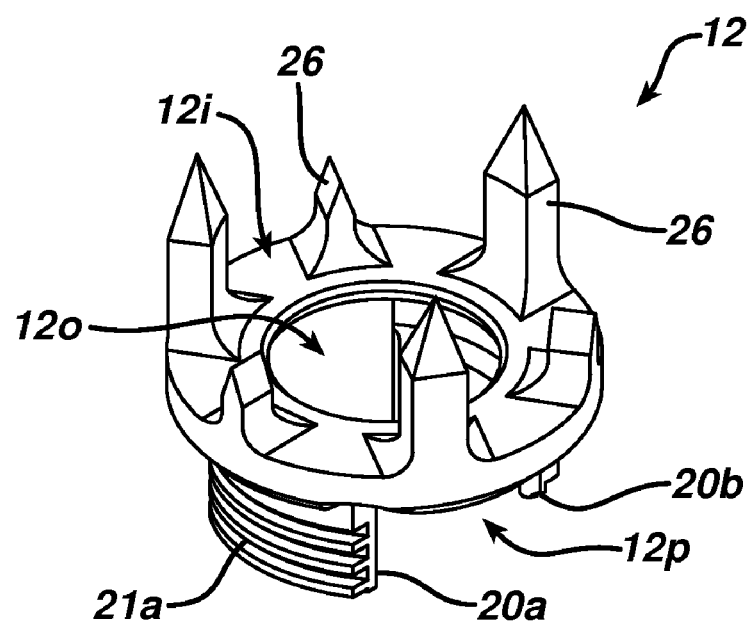
FIG. 2B is a bottom perspective view of the staple body shown in FIG. 2A.

The staple body 12 is shown in more detail in FIGS. 2A and 2B, and it can have a variety of configurations. In the illustrated exemplary embodiment, it has a substantially annular shape with a superior surface 12s, an inferior surface 12i, and a central opening 12o formed therethrough. The inferior surface 12i of the staple body 12 can include one or more bone-engaging members 26 formed thereon and adapted to extend into bone to prevent rotational movement of the staple 12 when the staple 12 is implanted. FIG. 2B illustrates multiple bone-engaging members 26 formed on and extending distally from the inferior surface 12i of the staple 12. The bone-engaging members 26 are in the form of spikes that are adapted to extend into bone, however they can have a variety of other shapes. As is further shown, the bone-engaging members 26 can vary in size. In use, a mallet or other device can be used to apply a force to the staple 12 to impact the spikes into bone at the desired implant site, or a fastening element can be used to drive the staple 12 into bone, as will be discussed in more detail below.

The central opening 12o in the staple body 12 can be adapted to receive a fastening element 14 therethrough to allow the fastening element 14 to mate the staple body 12 to bone. While the configuration of the central opening 12o can vary depending on the configuration of the fastening element 14, as will be discussed in more detail below with respect to FIG. 3, in one exemplary embodiment the central opening 12o has a substantially spherical, concave surface 22 formed therearound for seating a substantially spherical mating surface of the fastening element 14. The spherical surface 22 allows the fastening element 14 to be polyaxially movable with respect to the staple body 12, thereby allowing the fastening element 14 to be inserted into bone at an angle with respect to the staple body 12. A person skilled in the art will appreciate that the central opening 12o can have a variety of other configurations, and that the staple body 12 can include a fastening element integrally formed therewith or mated thereto. For example, the staple body 12 can be swaged such that the fastening element 14 is integrated to the staple body 12 while allowing the fastening element 14 to rotate with respect to the staple body 12 to allow insertion into bone.

As further shown in FIGS. 2A and 2B, the staple body 12 can also include opposed arms 20a, 20b formed on the superior surface 12s. As will be discussed in more detail below, the arms 20a, 20b can be adapted to couple to the locking assembly, thus the arms 20a, 20b can include a mating element formed thereof for mating with at least a portion of the locking assembly. As shown in FIGS. 2A and 2B, each arm 20a, 20b can include threads 21a, 21b formed on an external surface thereof. The threads 21a, 21b can extend along the entire length of each arm 20a, 20b, or they can be formed only on a terminal portion of the arms 20a, 20b, as shown. In one exemplary embodiment of the invention, the mating elements can have a square thread pattern. The particular configuration of each arm 20a, 20b can vary depending on the particular configuration of the locking mechanism, and a variety of other mating elements can be used to engage the locking assembly.

In use, the staple body 12 is adapted to seat a spinal fixation element. Accordingly, the superior surface 12s of the staple body 12 can define a pathway 12p formed between the opposed arms 20a, 20b. The pathway 12p can be adapted to seat a spinal fixation element between the opposed arms 20a, 20b such that the spinal fixation element extends across the superior surface 12s and the opening 12o. As a result, when the locking assembly is applied to the staple body 12, the spinal fixation element can be engaged between the locking assembly and the staple body 12 to maintain the spinal fixation element in a substantially fixed position. A person skilled in the art will appreciate that the pathway 12p can have a variety of configurations, and it can be linear or non-linear such that it changes direction, is tortuous, has curves or bends, etc.

The superior surface 12s of the staple body 12 can also include features to facilitate engagement of a spinal fixation element between the locking assembly and the staple body 12. By way of non-limiting example, the superior surface 12s can include one or more protrusions (not shown) formed thereon and adapted to extend into a spinal fixation element, such as a tether, an exemplary embodiment of which will be described in more detail below. In other embodiments, the superior surface 12s can include one or more ridges or grooves formed thereon for receiving one or more complementary grooves or ridges formed on the locking assembly. FIG. 2A illustrates two grooves 24a, 24b formed on opposed sides of the superior surface 12s of the staple body and positioned within the pathway 12p. The grooves 24a, 24b are adapted to receive complementary ridges formed on the washer of the locking assembly, as will be discussed in more detail with respect to FIGS. 4A and 4B.

Figure 3:
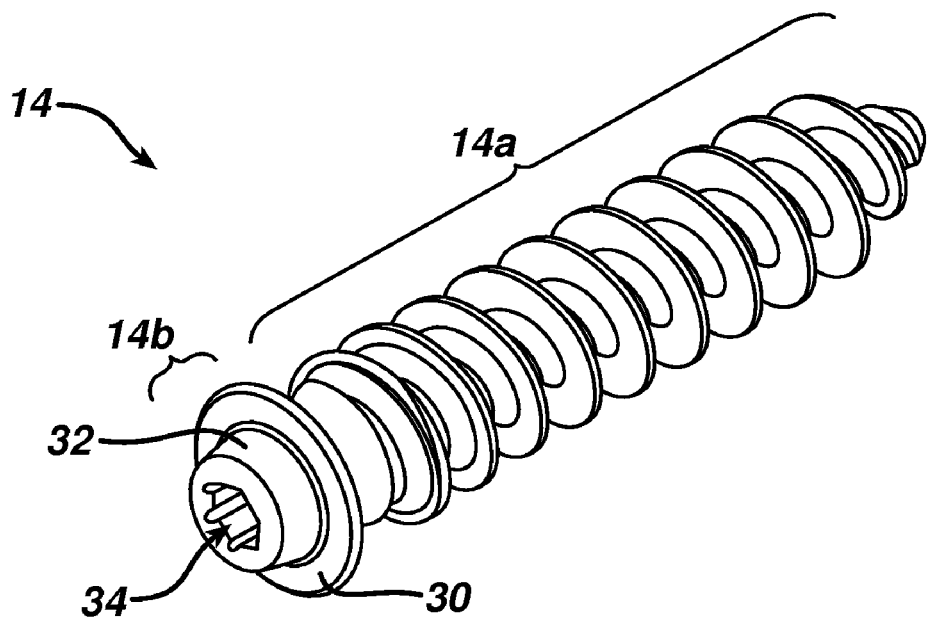
FIG. 3 is a perspective view a fastening element of the spinal anchoring device shown in FIG. 1A.

As previously mentioned, the staple body 12 can be adapted to receive a fastening element 14 through the central opening 12o. While the fastening element 14 can have a variety of configurations, FIG. 3 illustrates one exemplary fastening element 14 that is in the form of a bone screw having a head 14b and a threaded shaft 14a that is adapted to extend into bone. The thread form of the threaded shaft 14a is preferably adapted for fixation in cancellous bone, and in certain exemplary embodiments the surface of the threaded shaft 14a can be treated to promote bone apposition. Techniques known in the art for promoting bone apposition include anodization and coating with materials containing calcium phosphate, collagen, bone growth factors, etc. The head 14b of the fastening element 14 can vary in shape and size depending on the configuration of the staple body 12, but in the illustrated exemplary embodiment the head 14b includes a flange 30 that is adapted to sit within the opening 12o in the staple body 12. The flange 30 can have a diameter that is greater than a diameter of the central opening 12o formed in the staple body 12 to prevent passage of the flange 30 therethrough. The flange 30 can also include a substantially spherical inferior surface (not shown) to allow the fastening element 14 to move polyaxially with respect to the staple body 12, as previously discussed.

The head 14b of the fastening element 14 can also include a proximal extension 32 extending proximally from the flange 30. The proximal extension 32, which can be formed integrally with the shaft 14a of the bone screw 14, can include a recess 34 formed therein for receiving a tool adapted to drive the fastening element 14 into bone. The recess 34 can have any shape and size, but in the illustrated embodiment it has a hexagonal shape for receiving a hexagonal driver tool.

In use, when the fastening element 14 is disposed through the central opening 12o of the staple body 12, the proximal extension 32 can extend into the pathway 12p that seats a spinal fixation element, such as a flexible tether. Such a configuration is effective to create a bend or kink in the tether to substantially prevent sliding movement of the tether, or to otherwise facilitate engagement of the tether between the staple body 12 and the locking assembly. A person skilled in the art will appreciate that, while a polyaxial bone screw 14 is shown, the bone screw can be monoaxial or it can have a variety of other configurations. Other techniques for attaching the staple body 12 to bone may also be used.

As discussed with respect to FIGS. 1A and 1B, the spinal anchoring device 10 can also include a locking assembly that is adapted to mate to the staple body 12 to maintain a spinal fixation element, such as a tether, in a fixed position relative to the staple body 12. The configuration of the locking assembly can vary, and it can be formed from a single component or from multiple components. The locking assembly can also be separate from the staple body 12, or it can be coupled to the staple body and movable between an unlocked and a locked configuration. In the illustrated exemplary embodiment, the locking assembly includes a washer 16 and a locking nut 18. The washer 16 is adapted to couple to the staple body 12 such that the tether is positioned between the washer 16 and the superior surface 12s of the staple body 12, and the locking nut 18 can be adapted to mate to the arms 20a, 20b of the staple body 12 to lock the washer 16 to the staple body 12, thereby locking the tether therebetween.

Figure 4A:
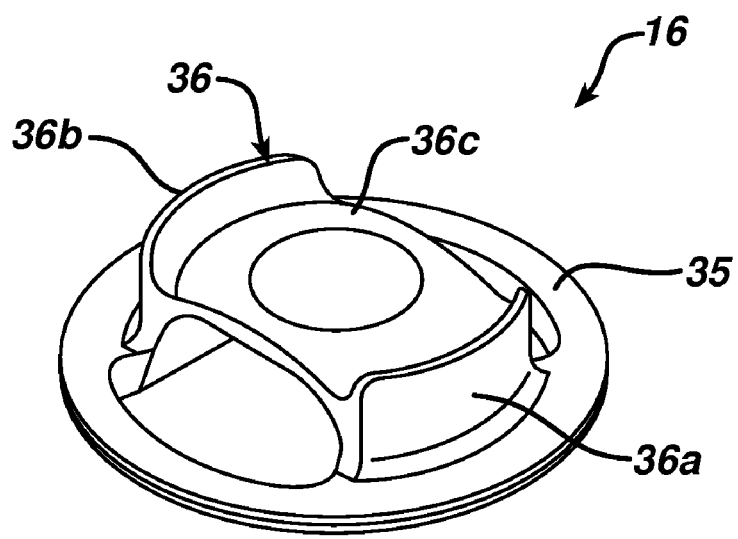
FIG. 4A is a top perspective view of a washer that forms part of the locking assembly of the spinal anchoring device shown in FIG. 1A.
Figure 4B:
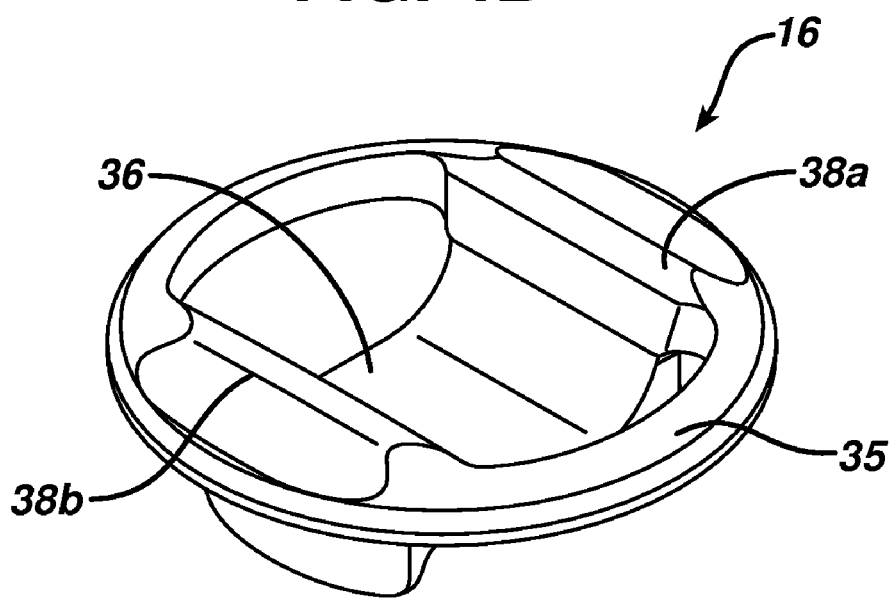
FIG. 4B is a bottom perspective view of the washer shown in FIG. 4A.

An exemplary washer 16 is shown in more detail in FIGS. 4A and 4B, and as shown the washer 16 includes a generally annular member 35 with a strut 36 spanning across the annular member 35. The annular member 35 is adapted to be positioned around the opposed arms 20a, 20b of the staple body 12, and thus it can have a size that substantially corresponds to the size of the annular portion of the staple body 12. The strut 36 is adapted to be received between the opposed arms 20a, 20b and positioned within the pathway 12p of the staple body 12 to substantially prevent rotation of the washer 16 with respect to the staple body 12. Such a configuration is particularly advantageous in that the tether is protected from high, damaging shear forces. The strut 36 can be adapted to merely facilitate positioning of the washer 16 with respect to the staple body 12, or it can be adapted to engage a spinal fixation element, such as a tether, disposed within the pathway 12p. In an exemplary embodiment, as shown, the strut 36 includes opposed legs 36a, 36b that extend outward from the annular member 35, and a connecting member 36c that extends between the opposed legs 36a, 36b. Such a configuration allows the connecting member 36c to be positioned a distance apart from the staple body 12, thereby allowing the extension 32 formed on the head 14b of the fastening element 14 to extend into the pathway 12p without abutting against the connecting member 36c of the strut 36. The height of the opposed legs 36a, 36b can, however, be varied based on the size of the spinal fixation element, and based on the intended use and whether the connecting member 36c is to engage the spinal fixation element. Moreover, the strut 36 itself can vary in shape and size depending on the configuration of the staple body 12 and the spinal fixation element adapted to be disposed therein.

As previously discussed with respect to the staple body 12, the washer 16 can also include features to facilitate engagement of a spinal fixation element, such as a flexible tether, between the staple body 12 and the washer 16. As shown in FIG. 4B, which illustrates the bottom of the washer 16, the annular member 35 of the washer 16 can include opposed ridges 38a, 38b formed thereon and adapted to be received with the complementary grooves 24a, 24b formed in the staple body 12, as shown in FIG. 2A. The ridges 38a, 38b are preferably formed adjacent to the legs 36a, 36b of the strut 36 such that when the strut 36 is received between the opposed arms 20a, 20b of the staple body 12, the ridges 38a, 38b are aligned with and extend into the grooves 24a, 24b. In use, when a flexible tether is disposed between the staple body 12 and the washer 16, the ridges 38a, 38b and grooves 24a, 24b will form a kink in the tether, thereby facilitating engagement such that the tether will be maintained in a substantially fixed position with respect to the device 10. A person skilled in the art will appreciate that a variety of other features can be used to facilitate engagement of a spinal fixation element. By way of non-limiting example, the washer 16 can include one or more protrusions or spikes formed on the surface thereof for abutting or extending into the tether.

Figure 5:
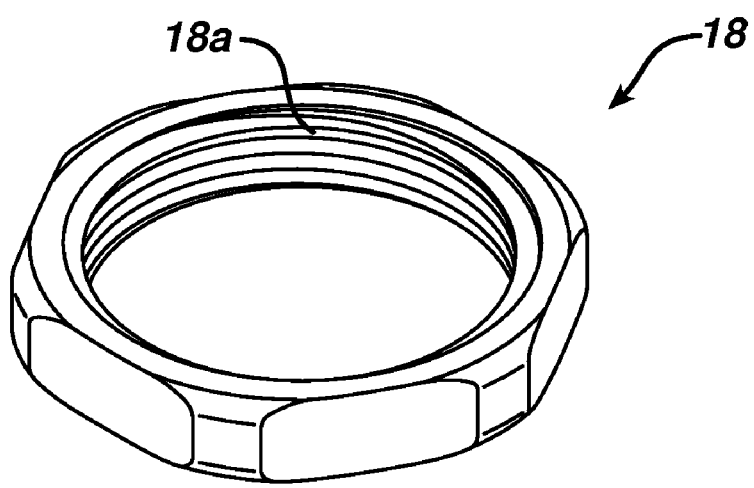
FIG. 5 is a perspective view of a locking nut that forms part of the locking assembly of the spinal anchoring device shown in FIG. 1A.

As previously noted, the locking assembly can also include a locking nut 18 that is adapted to lock the washer 16 to the staple body 12. An exemplary locking nut 18, shown in more detail in FIG. 5, has a generally annular shape. The locking nut 18 can, however, have an external surface that is hexagonal or of some other shape that allows the locking nut 18 to be engaged by a wrench or other driver tool for rotating the locking nut 18. In use, the locking nut 18 is adapted to be positioned around and to mate to the opposed arms 20a, 20b on the staple body 12. Accordingly, as previously indicated, the locking nut 18 can include threads 18a formed therein for mating with the corresponding threads 21a, 21b formed on the arms 20a, 20b of the staple body 12. In an exemplary embodiment, the locking nut 18 can be swaged to the washer 16 during manufacturing to integrate the two yet allow the nut 18 to be rotated with respect to the washer 16 during tightening of the closure mechanism. A variety of other mating techniques can also be used to mate the locking nut 18 to the body, including a snap-fit connection, an interference fit, etc.

A person skilled in the art will appreciate that the locking assembly can have a variety of other configurations. For example, rather than using a locking nut 18, the washer 16 itself can be adapted to mate to the staple body 12. The washer 16 can be a separate component, or it can be mated to the staple body 12 and movable between an open or unlocked position and a closed or locked position. For example, the washer 16 may be connected to the staple body 12 by a hinge or the like. Alternatively, the locking nut 18 can be used without the washer 16 to fix the tether to the staple body 12. In other embodiments, the locking nut 18 can be in the form of an inner set screw that mates to an inner surface of the legs 20a, 20b of the staple body 12.

Figure 6:
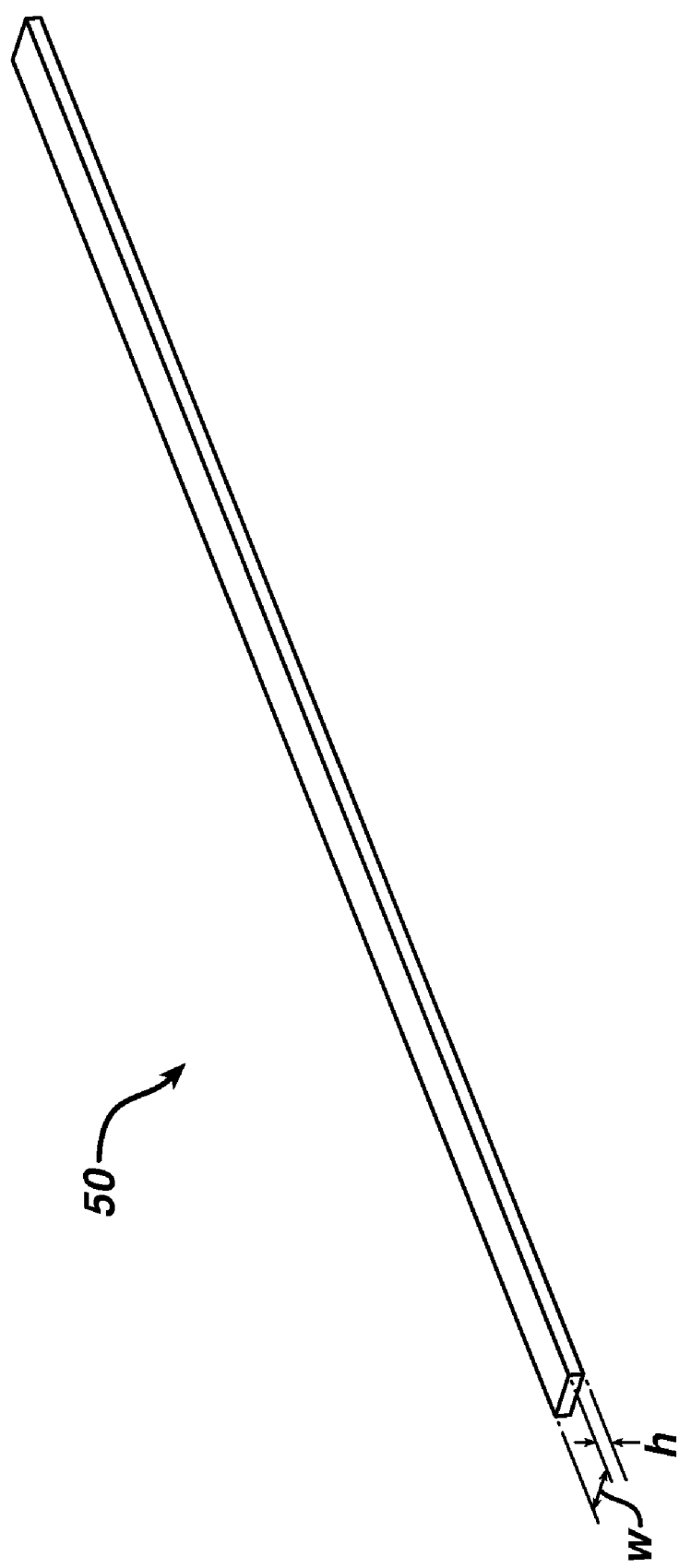
FIG. 6 is a perspective view of one exemplary embodiment of a flat flexible tether.

Referring back to FIGS. 1A and 1B, in use the device 10 is adapted to receive and engage a spinal fixation element. While a variety of spinal fixation elements can be used, including both flexible and rigid fixation elements, in an exemplary embodiment the spinal fixation element is a flexible tether. FIG. 6 illustrates one exemplary embodiment of a flexible tether 50, and as shown the tether 50 is substantially flat or planar. More particularly, the tether 50 can have a cross-sectional width w that is greater than a cross-sectional height h. In one exemplary embodiment, the width w can be at least two times greater than the height h. By way of non-limiting example, the width w can be in the range of about 4 mm to 8 mm, and preferably about 6 mm, and the height h can be in the range of about 0.5 mm to 2.5 mm, and preferably about 1.5 mm. Alternatively, the tether can have any number of different cross-sections, including square and round. In some preferred embodiments, the tether cross-section is square or round initially but then becomes flattened as the closure mechanism is tightened.

The tether 50 can be made using a variety of techniques, but in one exemplary embodiment it is made using a flat braiding process. Other suitable processes include, for example, a 3-D weaving process. The properties of the tether 50 can also vary, but in an exemplary embodiment the tether has a tensile strength in the range of about 1 GPa to 5 GPa, and preferably about 3 GPa, and a tensile modulus in the range of about 10 GPa to 200 GPa, and preferably about 100 GPa.

The materials used to form the tether can also vary, but suitable exemplary materials include polymers such as ultra-high molecular weight polyethylene (UHMWPE). Examples of commercially available UHMWPE fibers include Dyneema® (manufactured by DSM) and Spectra® (manufactured by Allied Signal). Other materials that can be used, for example, include polyethylene terephthalate (PET), nylon, Kevlar®, carbon, etc. In other embodiments, the tether 50 can be made from a combination of materials, for example UHMWPE fibers combined with PET fibers. The tether 50 can also be made from bioabsorbable materials, such as poly (L-lactic acid) or other high strength, slowly degrading materials known in the art.

In use, the tether 50 can be positioned within the pathway 12p of the staple body 12 after the staple body 12 is implanted in bone. An impacting tool for driving the staple body 12 into bone can be used to implant the staple 12. The fastening element 16 can then be inserted therethrough to fix the staple body 12 to the bone. Alternatively, a driver tool can be used to drive the fastening element 16 into bone, thereby driving the staple body 12 into bone. When the tether 50 is positioned in the pathway 12p, the tether 50 will extend between the legs 20a, 20b and up around the extension 32 on the fastening element 16. The washer 14 can then be placed around the legs 20a, 20b of the staple body 12, and the locking nut 16 can be threaded onto the legs 20a, 20b to lock the washer 16 to the staple body 12, thereby locking the tether 50 to the device 10. The ridges 38a, 38b on the washer 16 will extend toward the grooves 24a, 24b on the staple body 12, thereby creating a kink or bend in the tether 50, further facilitating engagement of the tether 50 between the washer 16 and the staple body 12. Other exemplary methods and tools for implanting the spinal anchoring device 10 will be discussed in more detail below.

FIGS. 7A-7F illustrate another exemplary embodiment of a spinal anchoring device 100. The device 100 is similar to spinal anchoring device 10 shown in FIG. 1A, and it includes a staple body 112, a fastening element 114, a washer 116, and a locking nut 118. In this embodiment, the washer 116 does not include a strut. Rather, the washer 116 includes opposed legs 136a, 136b that extend from a substantially planar annular body 135. The legs 136a, 136b each include a flange 137a, 137b formed on the terminal end thereof and extending in opposed directions from one another. The flanges 137a, 137b are adapted to engage the locking nut 118 to allow the washer 116 and locking nut 118 to be mated to one another prior to mating the locking assembly to the staple body 12. The legs 136a, 136b can be flexible to allow the locking nut 118 to be inserted there over and mated to the washer 116.

Figure 7C:
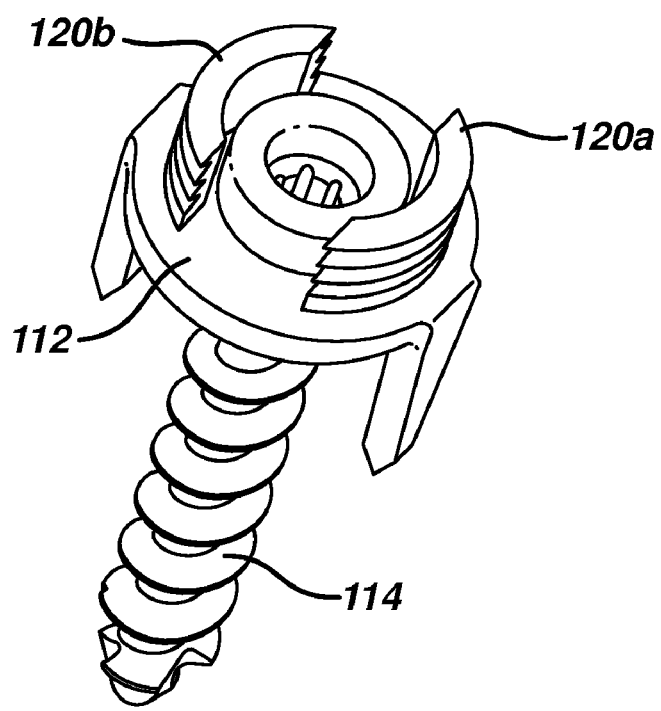
FIG. 7C is a perspective view of the spinal anchoring device shown in FIG. 7A without the tether and the locking mechanism coupled thereto.
Figure 7D:
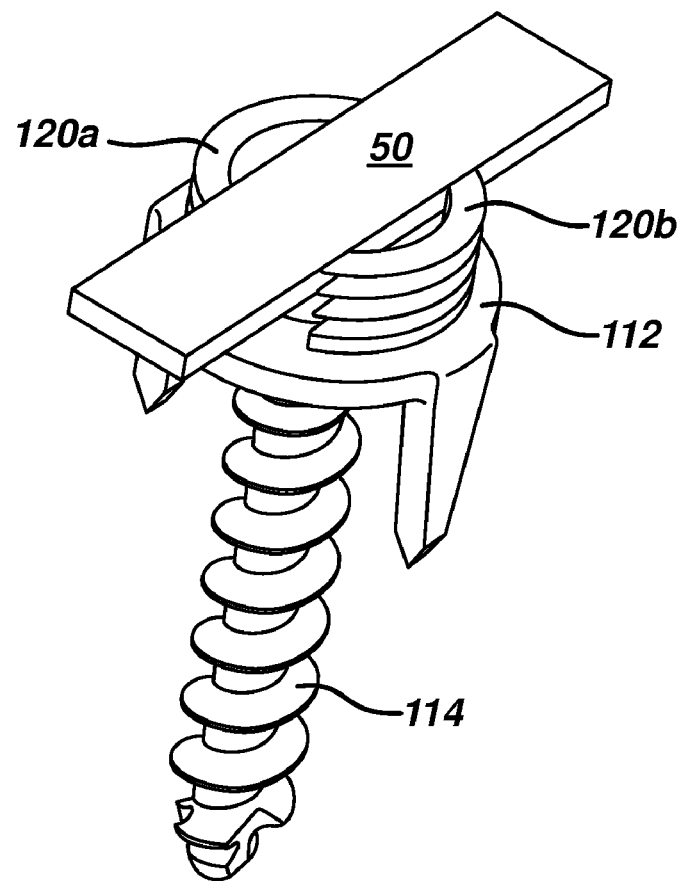
FIG. 7D is a perspective view of the spinal anchoring device shown in FIG. 7C showing the tether extending through a pathway formed therein.
Figure 7E:
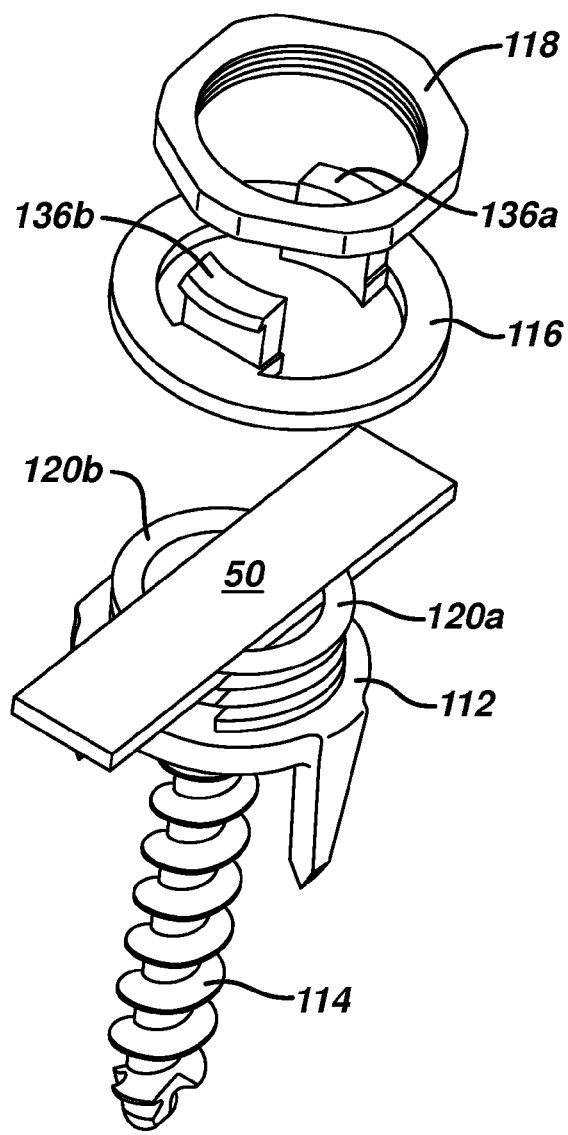
FIG. 7E is a perspective view of the spinal anchoring device shown in FIG. 7D showing the locking mechanism about to be coupled thereto and having a locking nut and a washer.
Figure 7F:
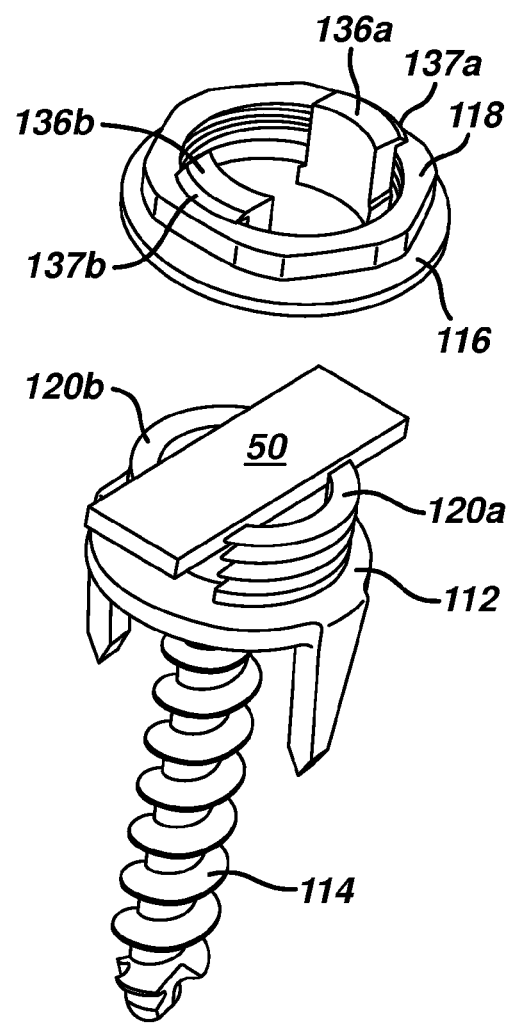
FIG. 7F is a perspective view of the spinal anchoring device shown in FIG. 7E showing the locking nut and washer of the locking mechanism coupled to one another.

FIGS. 7C-7F illustrate assembly of the device, and as shown the tether 50 is positioned in the pathway in the staple body 112. The washer 116 and locking nut 118 can be mated to one another, as shown in FIG. 7F, and then they can be mated to the staple body 112. The mating configuration of the washer 116 and the locking nut 118 allows the locking nut 118 to rotate freely with respect to the washer 116, thereby allowing the washer 116 to maintain a substantially fixed position with respect to the staple body 112, while the locking nut 118 is threaded onto the arms 120a, 120b of the staple body 112. This is particularly advantageous as the legs 136a, 136b of the washer 116 will be positioned between the arms 120a, 120b of the staple body 112, thereby preventing the washer 116 from rotating with respect to the staple body 112.

Figure 8:
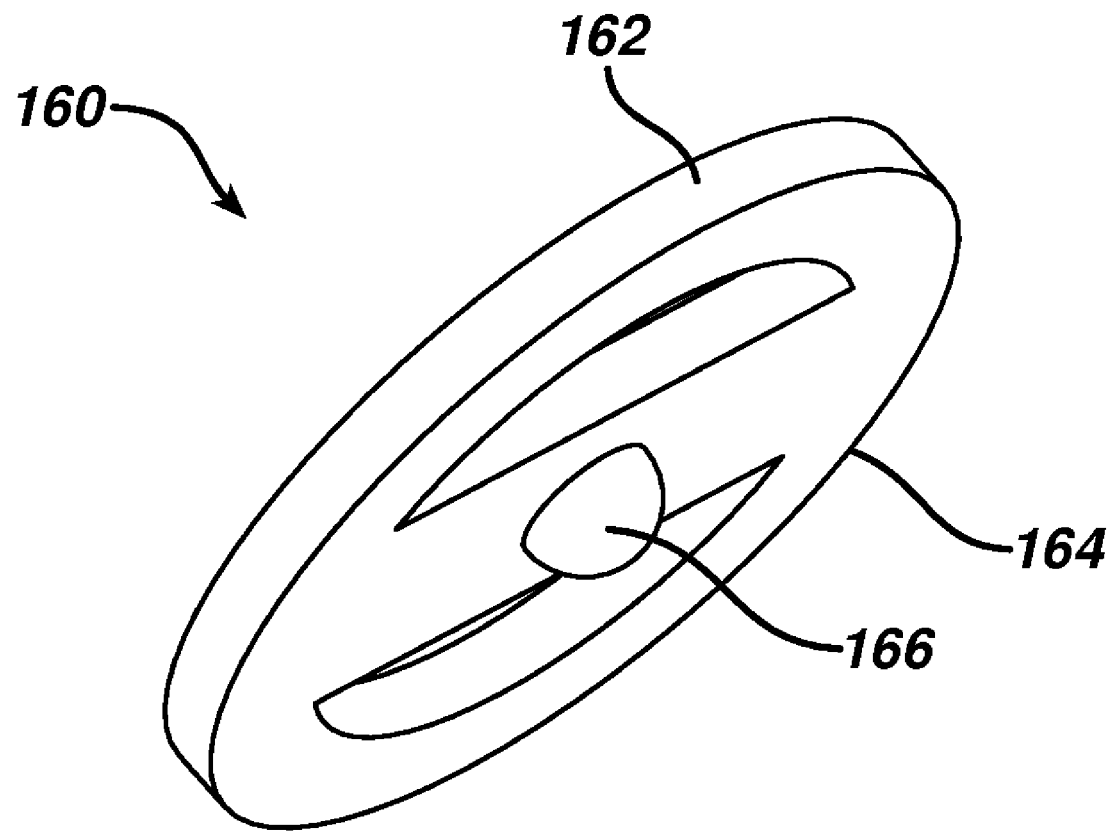
FIG. 8 is a perspective view of another embodiment of a washer for use with a spinal anchoring device.

FIG. 8 illustrates another exemplary embodiment of a washer 160 for use with a spinal anchoring device. In this embodiment, the washer 160 has a substantially planar annular member 162 with a substantially planar strut 164 extending thereacross. The washer 160 also includes a tether-engaging protrusion 166 formed thereon. In use, the opposed arms of a staple body, such as arms 20a, 20b of staple 12 shown in FIG. 1A, are adapted to be received within the annular member 162 such that the strut 164 extends between the opposed arms 20a, 20b. The planar configuration of the washer 160 will cause the washer 160 to engage the tether 50 between the staple body 12 and the washer 160. As a result, the protrusion 166 formed on the strut 164 will abut and deform the tether 50, thereby engaging the tether 50 to substantially prevent movement of the tether 50 with respect to the device. Since the washer 160 is substantially planar, the head of the fastening element used with the staple body preferably does not extend into the tether pathway formed in the staple body, as such a configuration would cause the strut 164 to abut against the head of the fastening element.

FIGS. 9A-9D illustrate yet another embodiment of a spinal anchoring device 200. In general, the device 200 includes a staple body 212, fastening element 214, and a locking nut 218 that are similar to staple body 12, fastening element 14, and locking nut 18 shown in FIG. 1A. In this embodiment, rather than using a washer 16 to engage a tether 50, a clip 216 is used to engage the tether 50. The clip 216 can be adapted to be disposed around a spinal fixation element, such as tether 50, and it can be adapted to be positioned within the pathway of the staple body 12 and disposed between the staple body 12 and the locking nut 218. While the shape and size of the clip 216 can vary depending on the shape and size of the spinal anchoring device used therewith, in an exemplary embodiment the clip 216 has a substantially elongate shape with opposed arms 216a, 216b that define a track or recess therebetween for seating the tether 50.

In use, the arms 216a, 216b can extend around the tether 50 to engage the tether 50. In an another exemplary embodiment, the clip 216 can be formed from a pliable or deformable material to allow the clip 216 to deform around the tether 50 when the locking nut 18 is applied to the staple body 12. FIG. 9C illustrates the clip 216 disposed around the tether 50 with the locking nut 218 about to be mated to the staple body 212. FIG. 9D illustrates the locking nut 218 threaded onto the staple body 212, and as shown the clip 216 is deformed by the locking nut 218 such that the clip 216 engages the tether 50 to prevent sliding movement thereof relative to the device 200. In another embodiment, the clip is a deformable tube that serves to protect the tether while tightening the locking nut. In yet another embodiment, the clip does not deform upon tightening the locking nut, thereby allowing the tether to slide within the closure mechanism.

FIGS. 10A-10C illustrate yet another exemplary embodiment of a spinal anchoring device 300. The device 300 includes a staple body 312 and fastening element 314 that are similar to staple body 12 and fastening element 14 shown in FIG. 1A. However, the staple body 312 does not include opposed arms formed thereon, but rather has a substantially planar superior surface 312s, and the fastening element 314 has a substantially planar head 314a formed thereon such that the head 314a is co-planar with, or recessed with respect to, the superior surface 312s of the staple body 312. The staple body 312 also includes several mating elements formed thereon for mating to the locking assembly. While the mating elements can have a variety of configurations, in the exemplary embodiment illustrated in FIGS. 10A-10C the staple body 312 includes cut-outs 312a, 312b, 312c, 312d formed therein for receiving tabs formed on the locking mechanism.

As shown, the locking mechanism includes first and second members 316a, 316b that are adapted to mate to opposed sides of the superior surface 312s of the staple body 312 to engage the tether 50 therebetween. While not shown, the first and second members 316a, 316b can be integrally formed as a single member that mates to the staple body 312. Each members 316a, 316b can have a substantially semi-circular shape with mating elements formed thereon for engaging the complementary corresponding mating elements formed on the superior surface 312s of the staple body 312. In the illustrated exemplary embodiment, the members 316a, 316b each includes two tabs formed thereon. Only two tabs 317a, 317b are shown formed on the first member 316a. Each tab 317a, 317b is adapted to extend into the corresponding cut-out 312a, 312b, 312c, 312d formed in the staple body 312 to engage the staple body 312 by a snap-fit or interference fit.

In use, a tether 50 can be positioned across the staple body 312, e.g., in the pathway, and the first and second members 316a, 316b can then be mated to the staple body 312, as shown in FIG. 10C, to engage the tether 50 therebetween. In an exemplary embodiment, each member 316a, 316b is positioned such that the tabs 317a, 317b are positioned on opposed sides of the tether 50, thereby allowing the annular portion of the members 316a, 316b to engage the tether 50. As is further shown in FIGS. 10B and 10C, the tether 50 can optionally be twisted to form one or more twists 51 between the two members 316a, 316b, thereby further preventing slidable movement of the tether 50 with respect to the device 300.

A person skilled in the art will appreciate that the spinal anchoring device can have a variety of other configurations, and it can include a combination of various features disclosed herein, as well as other features to facilitate engagement of a spinal fixation element, such as a tether.

Figure 11A:
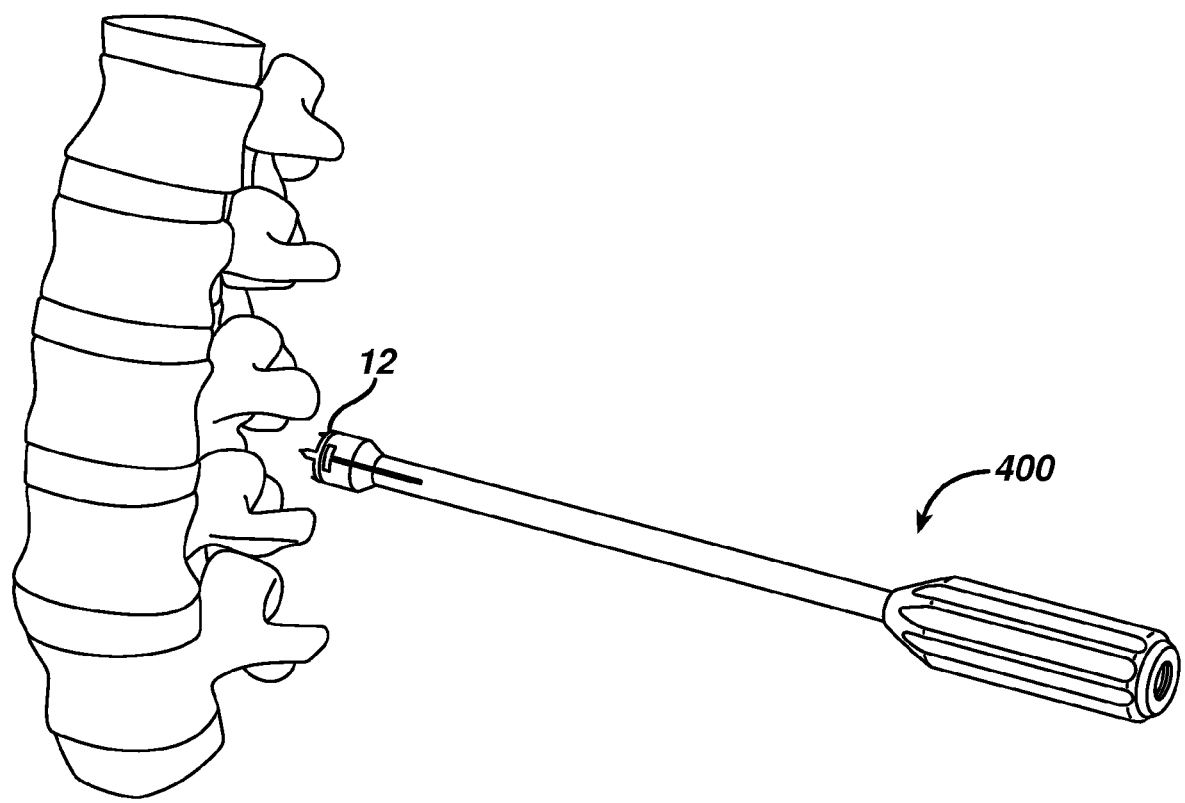
FIG. 11A is an illustration showing a staple inserter tool about to implant a staple of a spinal anchoring device in a vertebra.
Figure 11B:
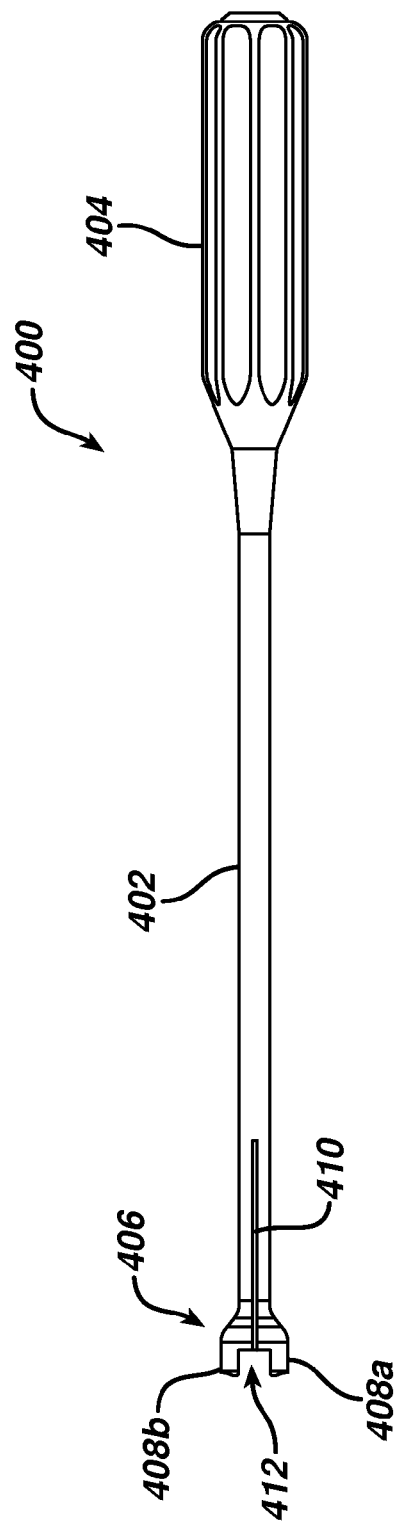
FIG. 11B is a perspective view of the staple inserter tool shown in FIG. 11A.
Figure 11C:
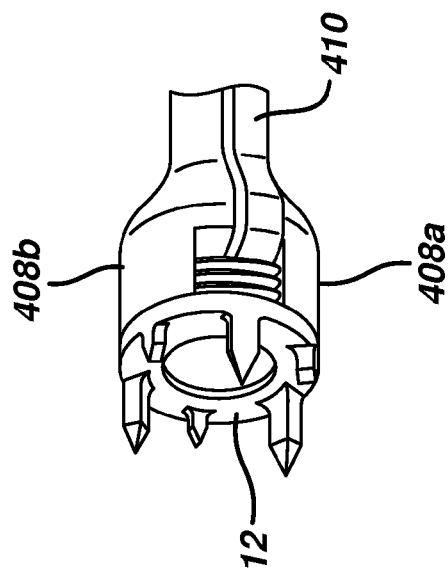
FIG. 11C is a perspective view of a distal end of the staple inserter tool shown in FIG. 11B with a staple coupled thereto.

An exemplary method for implanting a spinal anchoring device is also provided. While the method can be performed using a variety of different spinal anchoring devices, the method is described in connection with spinal anchoring device 10. Referring first to FIG. 11A, a staple inserter 400 is shown for inserting the staple body 12 of device 10 into bone. The exemplary staple inserter 400, shown in more detail in FIG. 11B, includes a generally elongate hollow shaft 402 having a proximal end with a handle 404 formed thereon, and a distal end with a staple-engaging member 406 formed thereon. The staple-engaging member 406 is adapted to engage the staple body 12, to allow the body 12 to be positioned relative to a vertebra, as shown in FIG. 11A, and driven into the vertebra. While the shape and size of the staple-engaging member 406 can vary depending on the shape and size of the staple body 12, in an exemplary embodiment the staple-engaging member includes opposed deflectable members 408a, 408b that are separated by an elongate slot 410. The elongate slot 410 extends proximally from the distal-most end of the device 400 to allow the opposed deflectable members 408a, 408b to deflect relative to one another. The length of the elongate slot 410 can vary depending on the desired flexibility of the deflectable members. As is further shown in FIGS. 11B and 11C, the opposed deflectable members 408a, 408b can include a substantially cylindrical distal portion having a recess 412 formed in a distal surface thereof for receiving the staple body 12. In the illustrated embodiment, the recess 412 has a substantially rectangular shape for receiving the arms 20a, 20b formed on the staple body 12, as shown in FIG. 11C.

In use, the staple body 12 can be engaged by the opposed deflectable members 408a, 408b by placing the deflectable members 408a, 408b over the staple body 12, thereby causing the members 408a, 408b to deflect around the arms 20a, 20b to engage the arms 20a, 20b. The staple inserter tool 400 can then be manipulated to place the staple 12 into a vertebrae. In one embodiment, the handle 404 of the tool 400 can be impacted to impact the staple body 12 into bone. Alternatively, the fastening element 14 can be used to drive the staple 12 into bone.

Figure 12A:
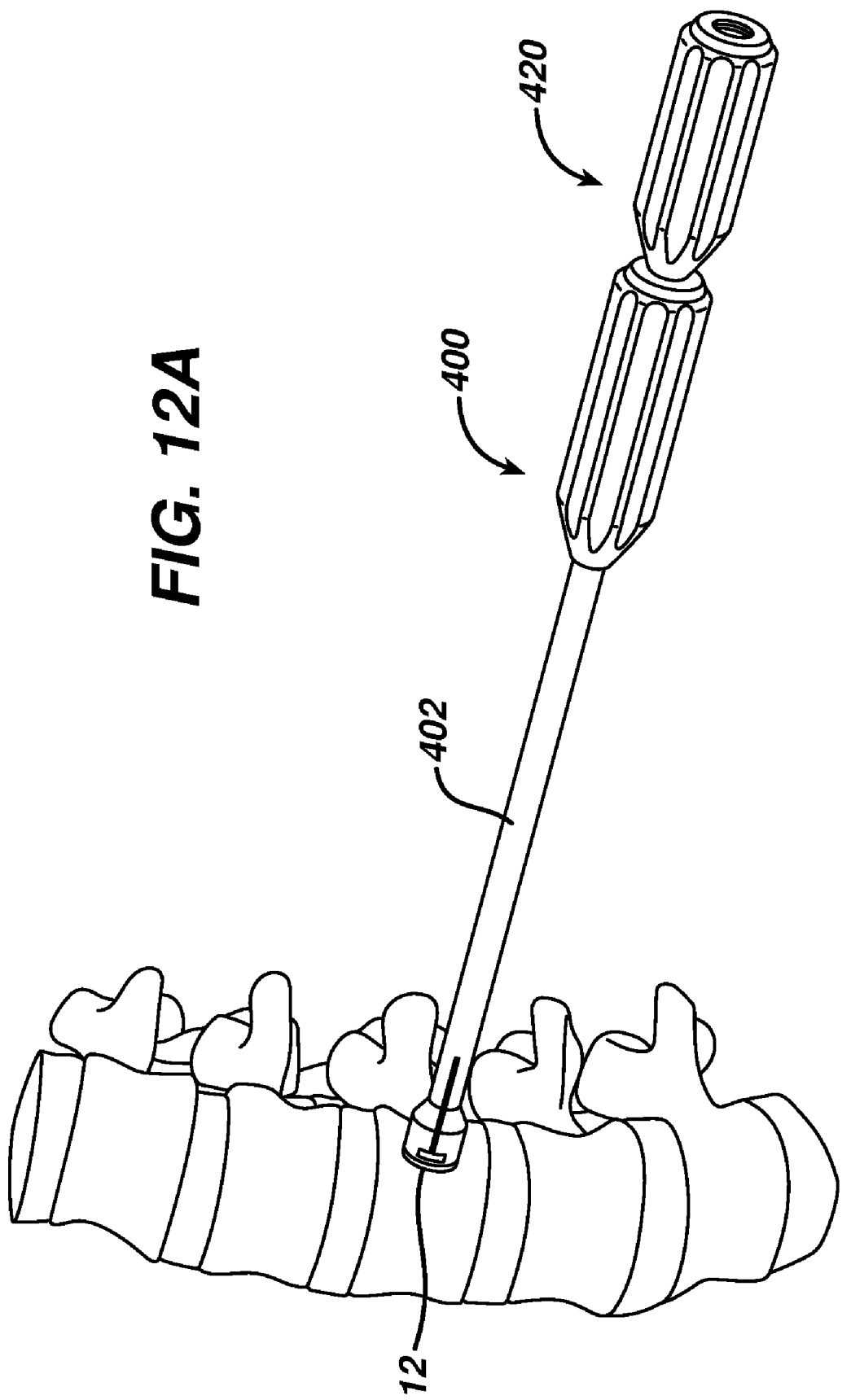
FIG. 12A is an illustration showing an awl inserted through the staple inserter tool and staple shown in FIG. 11A for preparing a bone hole.

Once the staple is implanted in the vertebra, or at least positioned as desired relative to the vertebra, one or more bone preparation tools can be inserted through the shaft 402 of the inserter tool 400 to prepare a bone hole for receiving the fastening element 14. By way of non-limiting example, FIG. 12A illustrates an awl 420 inserted through the hollow elongate shaft 402 of the inserter tool 400. The awl 420 is shown in more detail in FIG. 12B, and as shown it has a generally elongate shaft 422 with a proximal handle 424 and a distal bone-penetrating tip 426 for starting a bone hole. FIG. 12C illustrates the distal end of the inserter tool 400 showing the bone-penetrating tip 426 of the awl 420 extending through the central opening in the staple body 12. In use, the awl 420 is inserted through the inserter tool 400 and an impacting force is applied to the handle 424 to drive the bone-penetrating tip 426 into bone. Consequently, the driving force applied to the awl 420 can be used to drive the staple body 12 into bone as well.

Figure 13A:
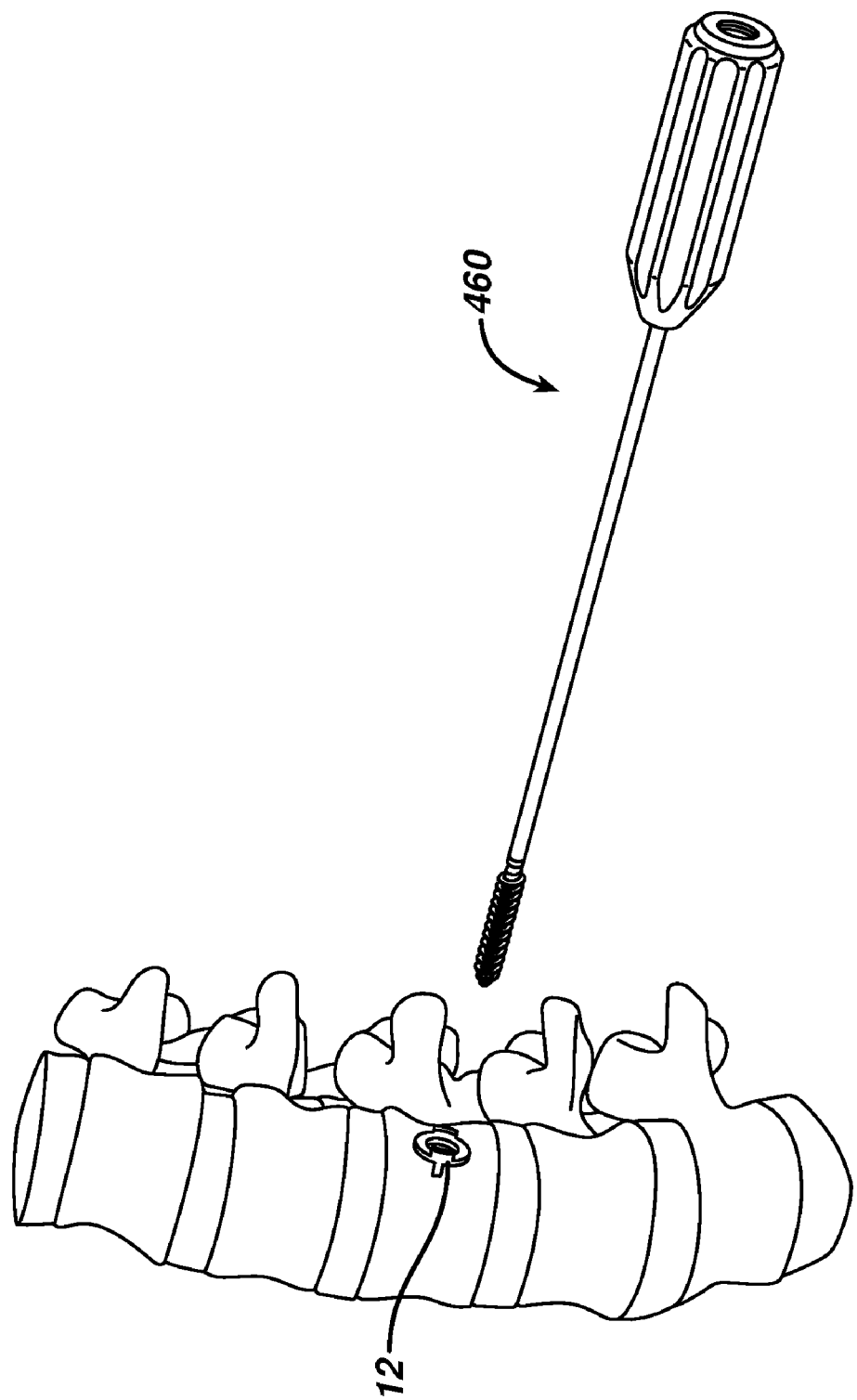
FIG. 13A is an illustration showing a tap about to be inserted through the staple implanted in the vertebrae for forming threads in the bone hole prepared by the awl.
Figure 13B:
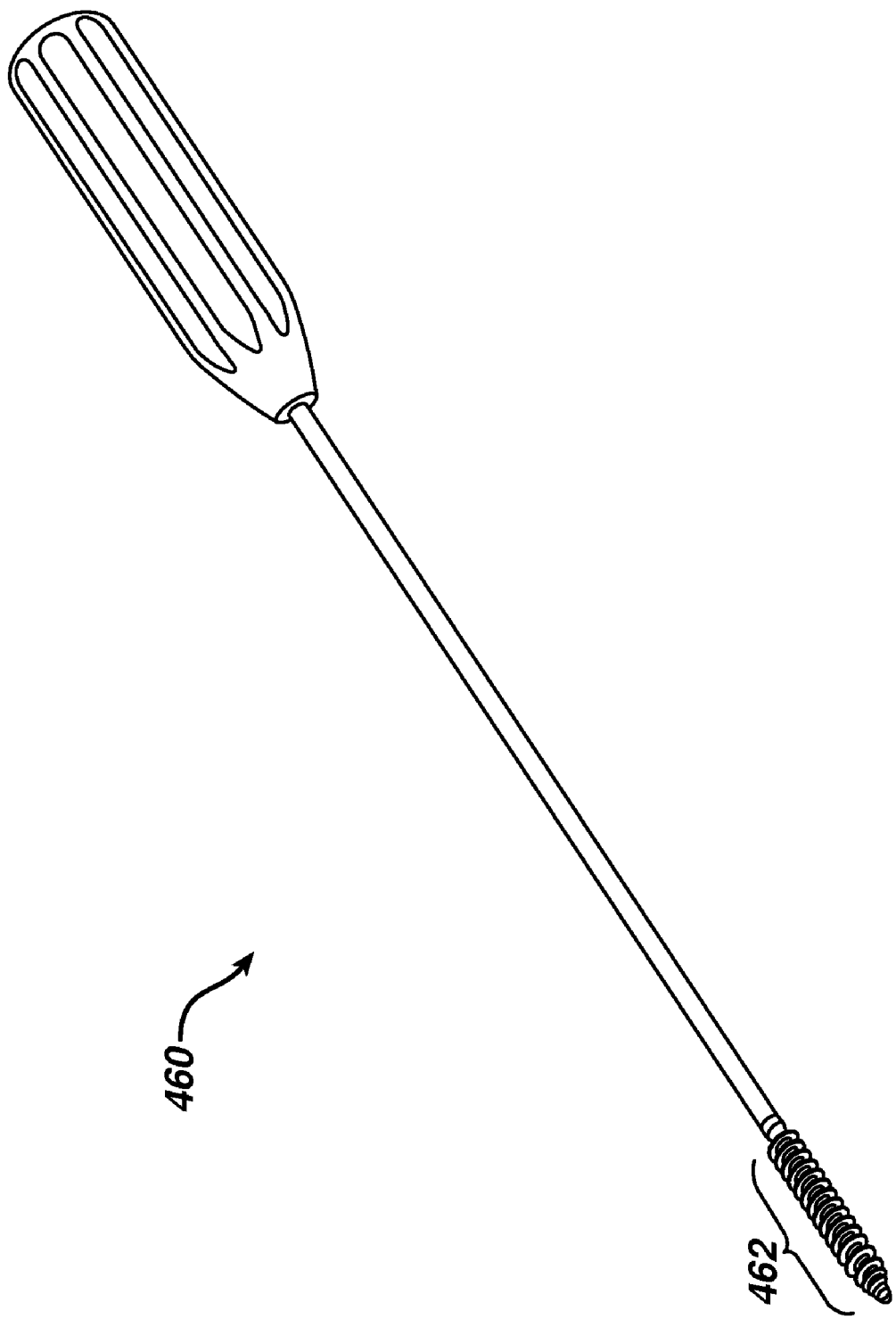
FIG. 13B is a perspective view of the tap shown in FIG. 13A.

Once the bone hole is prepared in the vertebra through the staple body 12, the staple inserter tool 400 and awl 420 can be removed, leaving the staple implanted in the vertebrae. A tap 460 can then be used to form threads within the bone hole, as shown in FIG. 13A, thereby preparing the bone hole for receiving the fastening element 14. The tap 460, which is shown in more detail in FIG. 13B, is similar to the awl 420 except that it includes a threaded shaft 462 formed on the distal end thereof. Alternatively, the tap can be inserted through the staple inserter to form threads within the bone hole.

Figure 14:
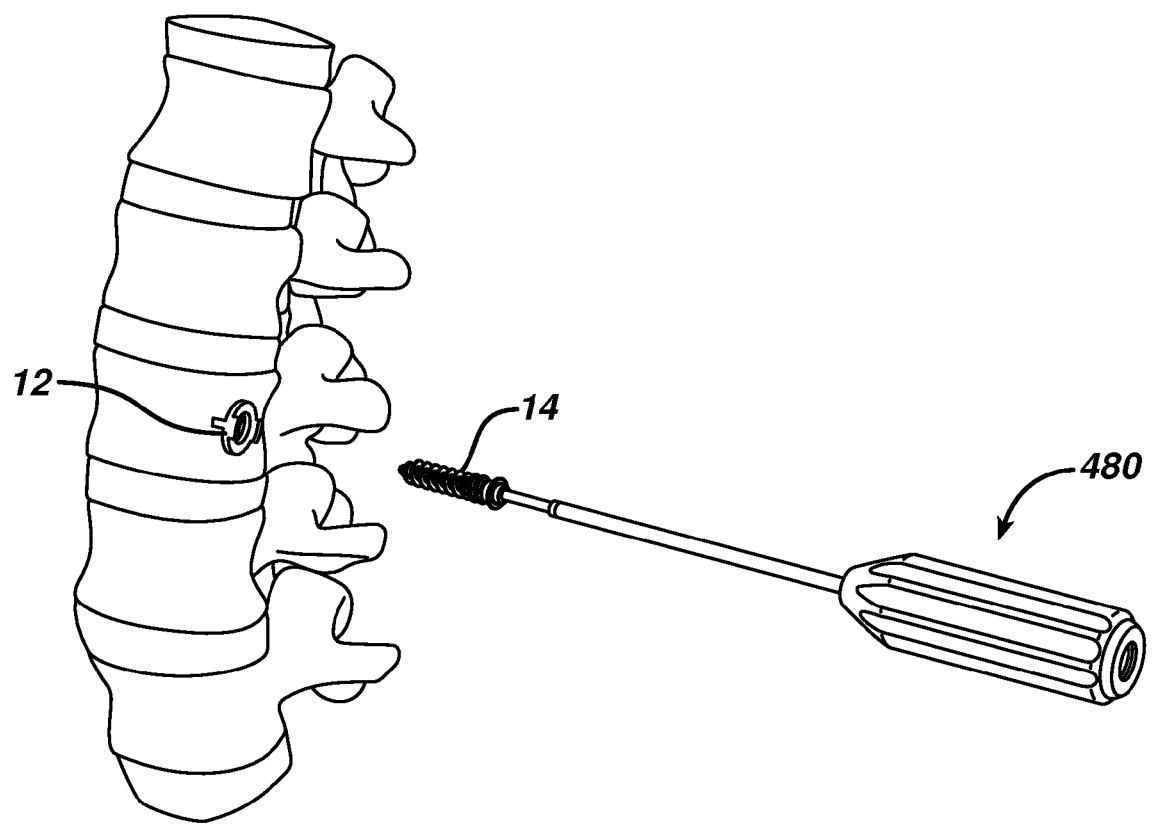
FIG. 14 is an illustration showing a driver tool about the implant a fastening element through the staple and into the bone hole.
Figure 15:
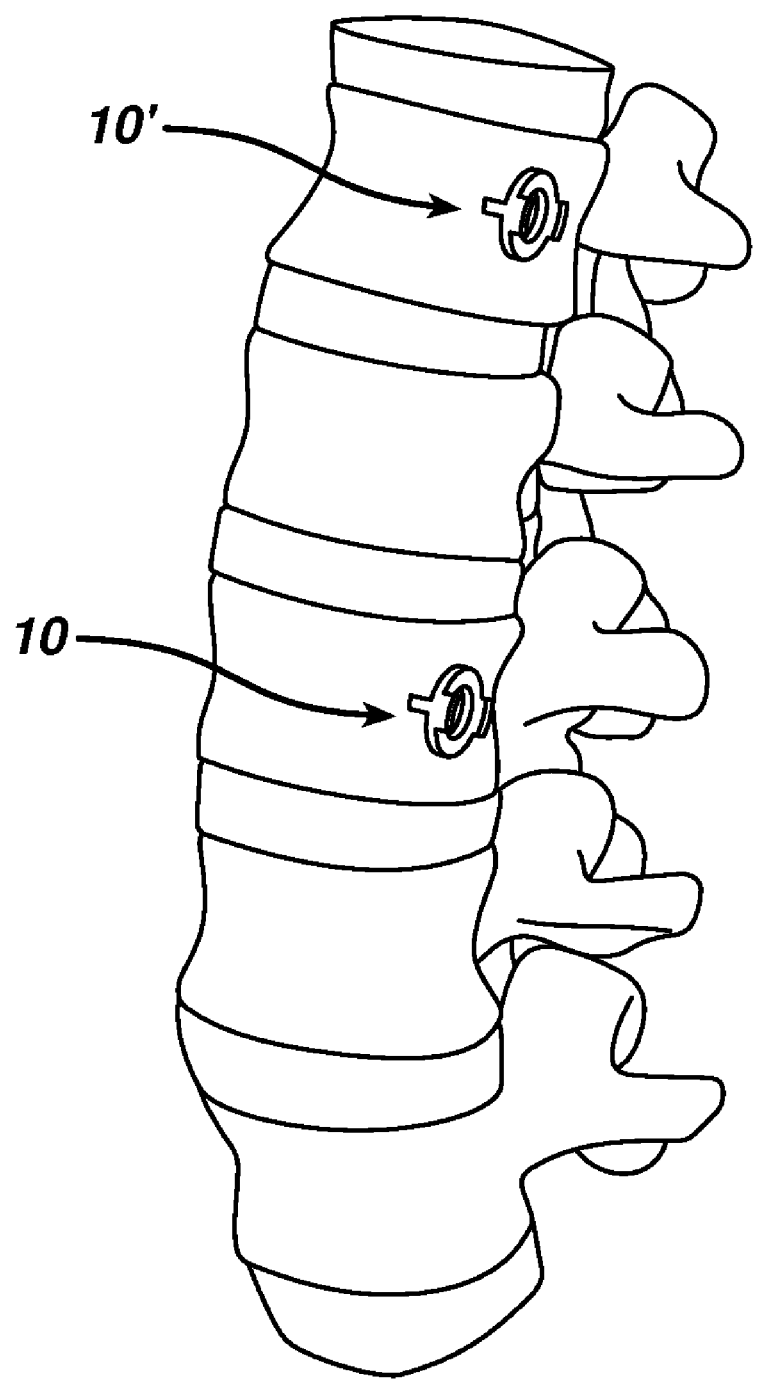
FIG. 15 is an illustration showing two spinal anchoring devices implanted in two vertebrae.

Once the bone hole is prepared using the awl 420, tap 460, and/or any other tools that may be necessary, the fastening element 14 can be inserted through the staple body 12 and into the bone hole to fixedly secure the staple body 12 to the vertebra. FIG. 14 illustrates the fastening element 14 about to be inserted into the bone hole using a driver tool 480. This procedure can be repeated to implant additional spinal anchoring devices one or more adjacent vertebrae. FIG. 15 shows two spinal anchoring devices 10, 10' implanted in two vertebrae in a patient's spinal column.

Figure 16B:
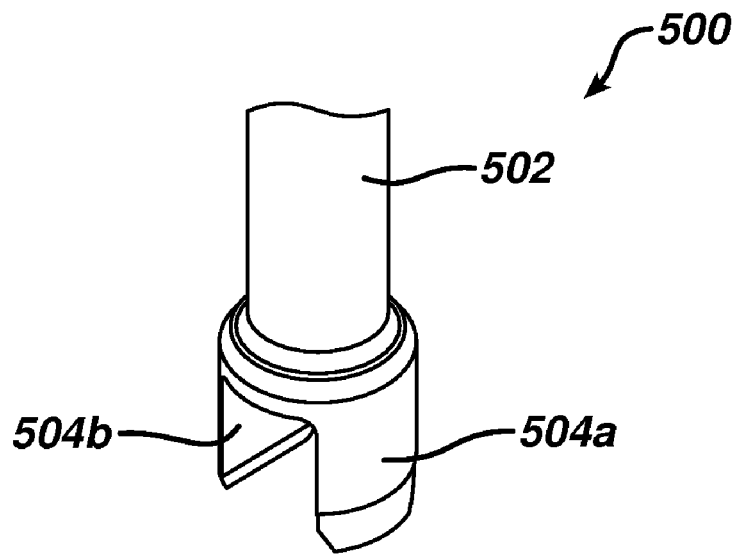
FIG. 16B is a perspective view of the fastener inserter tool shown in FIG. 16A.
Figure 16C:
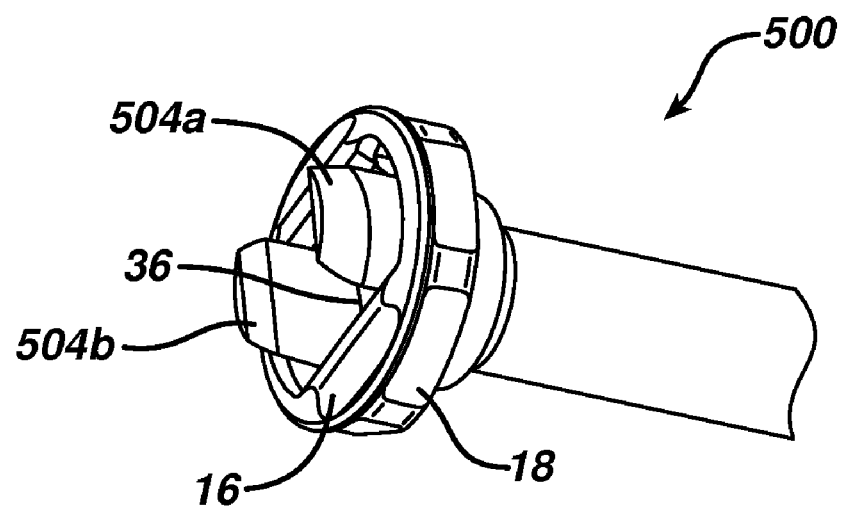
FIG. 16C is a perspective view of a distal portion of the fastener inserter tool shown in FIG. 16B showing a fastening element coupled thereto.

Once a desired number of spinal anchoring devices are implanted, a spinal fixation element, such as tether 50, can be positioned to span between each of the devices. FIG. 16A illustrates tether 50 extending between spinal anchoring devices 10, 10'. A locking assembly can then be applied to each spinal anchoring device 10, 10' to lock the tether 50 relative thereto. A fastener inserter tool 500 can be used to apply the fastening element, e.g., the washer 16 and locking nut 18, as is also shown in FIG. 16A. The exemplary inserter tool 500, which is shown in more detail in FIGS. 16B and 16C, has a generally elongate shaft 502 with a distal end having a substantially cylindrical shape with opposed arms 504a, 504b formed thereon. The arms 504a, 504b are adapted to receive and engage the strut 36 of the washer 16, thereby mating the washer 16, as well as the locking nut 18 which is disposed around the washer 16, to the inserter tool 500. The inserter tool 500 can then be manipulated to position the washer 16 and locking nut 18 over the arms 20a, 20b of the staple body 12.

Figure 17A:
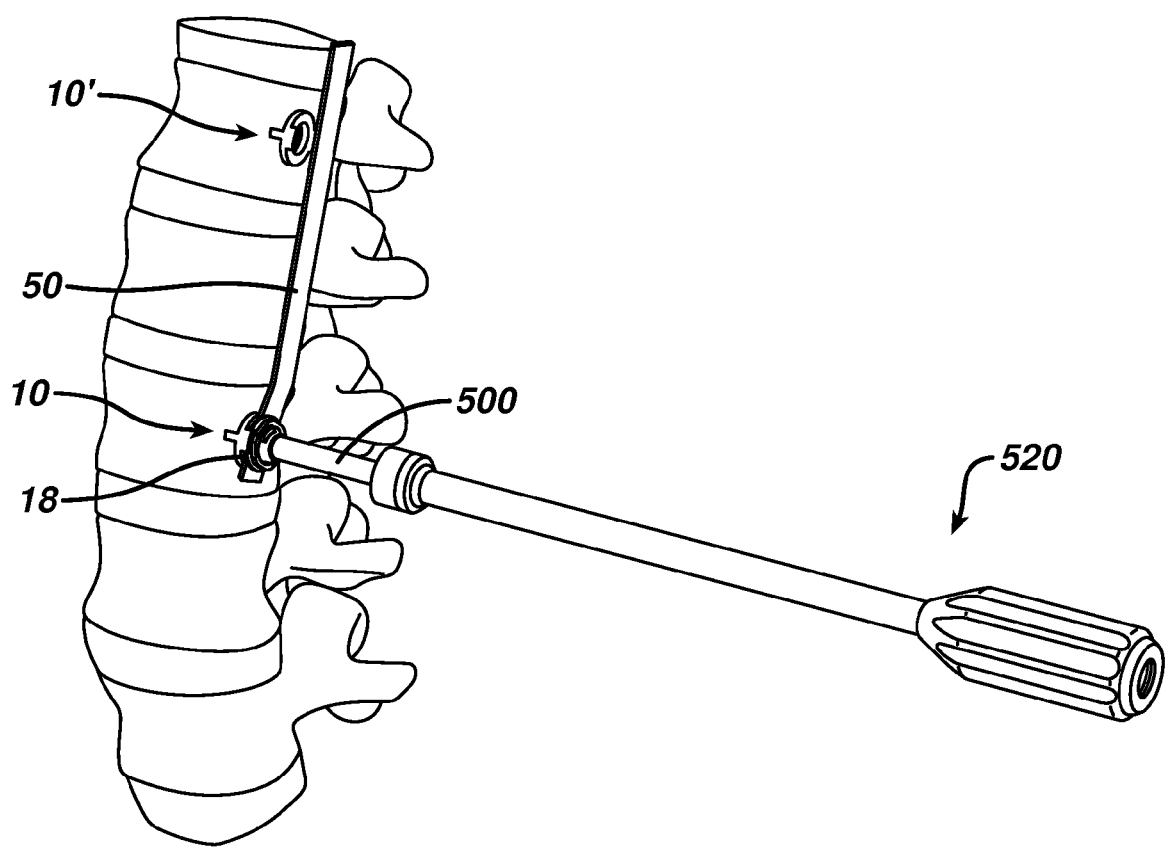
FIG. 17A is an illustration showing the fastening element applied to the spinal anchoring device using the fastener inserter tool shown in FIG. 16A, and showing a wrench inserted over the driver.
Figure 17B:
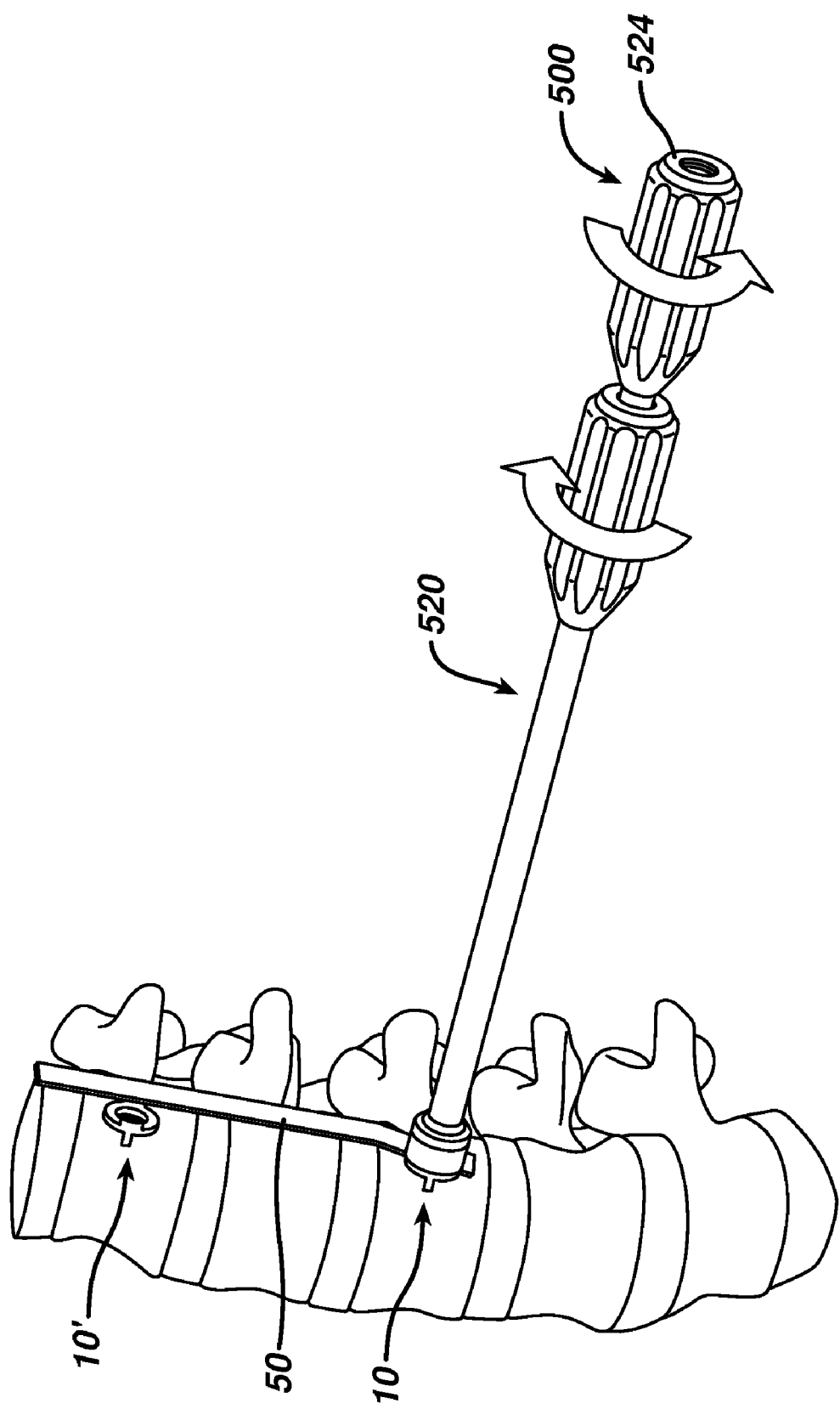
FIG. 17B is an illustration showing the wrench of FIG. 17A being rotated relative to the drive to rotate a locking nut of the locking mechanism.
Figure 17C:
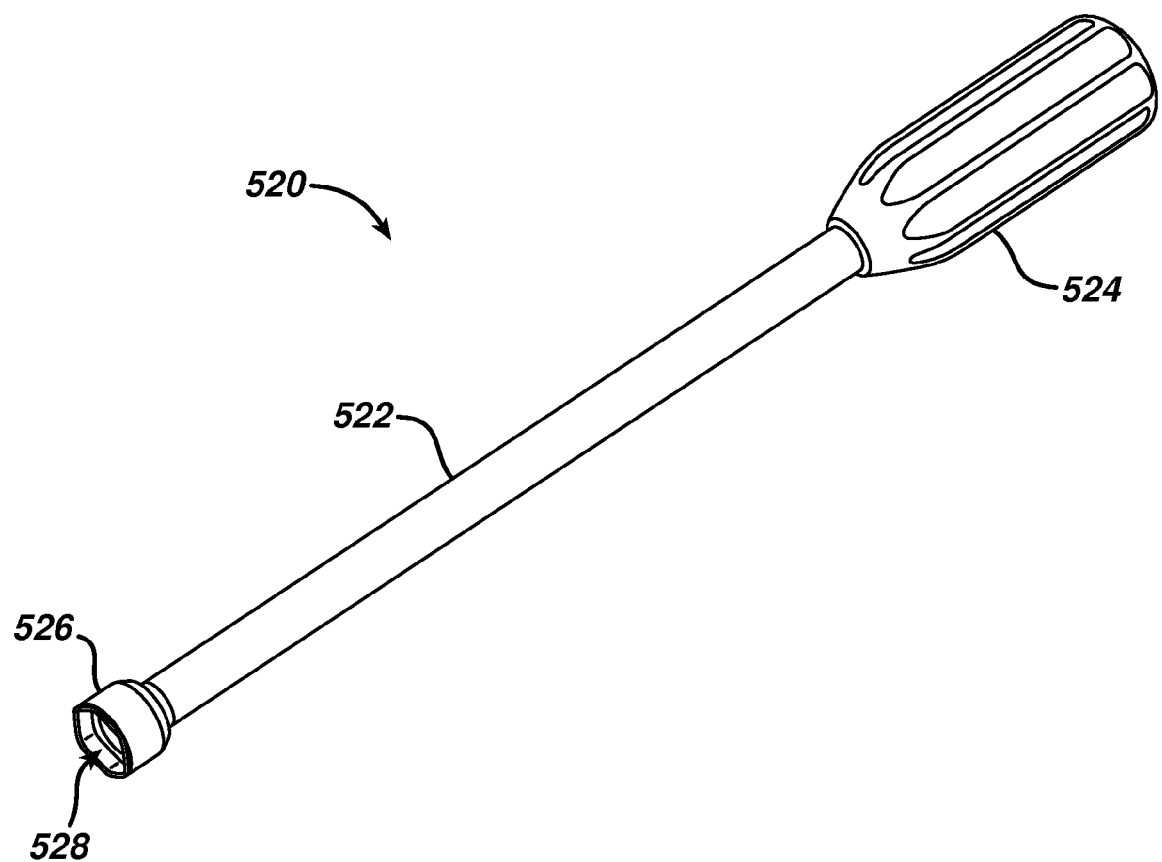
FIG. 17C is a perspective view of the wrench shown in FIGS. 17A and 17B.
Figure 18:
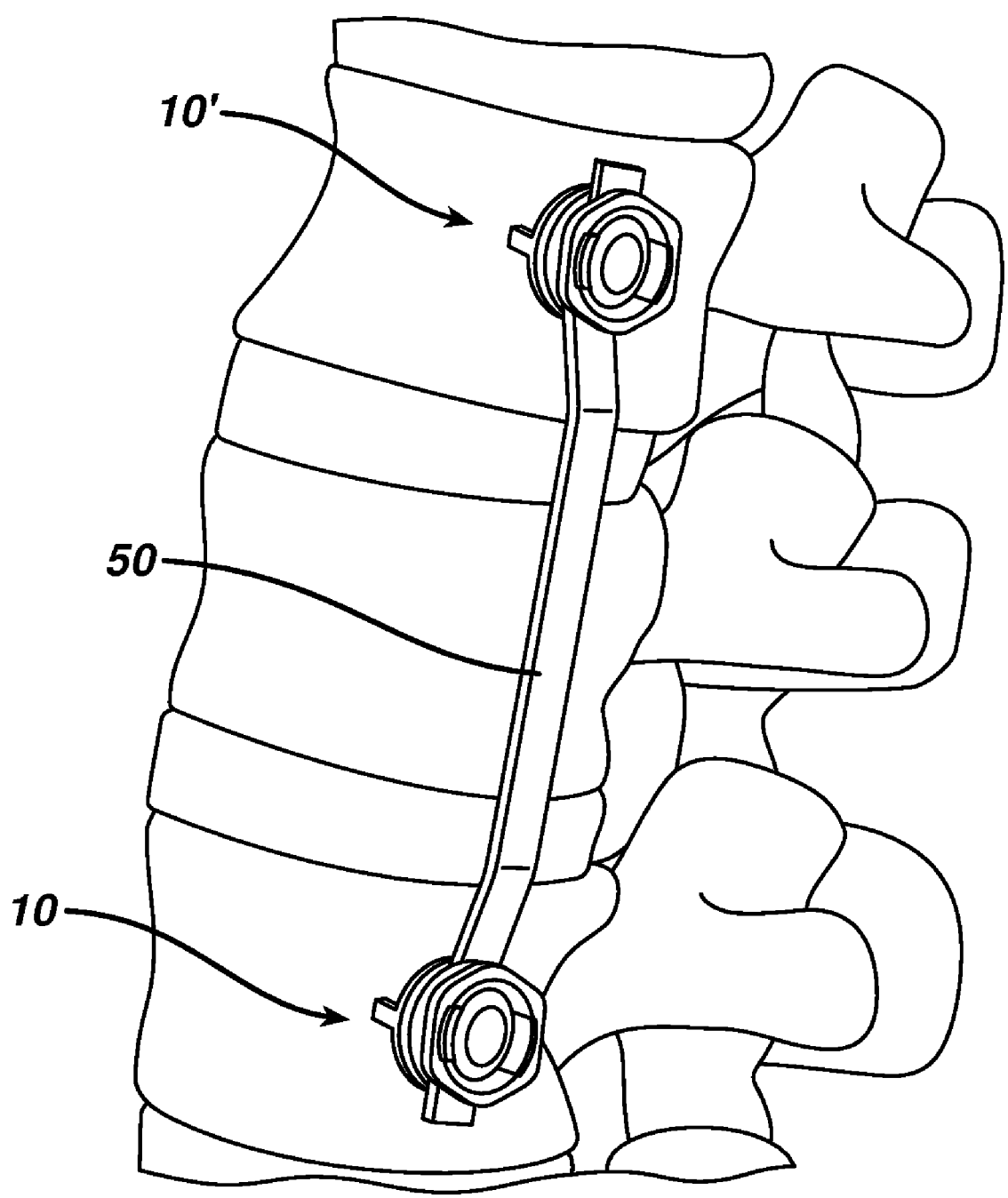
FIG. 18 is an illustration showing a tether extending between and coupled to two spinal anchoring devices implanted in two vertebrae.

The fastener inserter tool 500 can also include a wrench 520 that is adapted to be slidably disposed over the fastener inserter tool 500 and that is adapted to engage and rotate the locking nut 18, as shown in FIGS. 17A and 17B. The wrench 520 is shown in more detail in FIG. 17C, and as shown it has a generally elongate hollow shaft 522 with a proximal handle 524 and a distal socket member 526 formed thereon. The socket member 526 includes a socket 528 formed therein and having a shape that corresponds to a shape of the locking nut 18. In an exemplary embodiment, the socket member 526 includes a hexagonal socket 528 formed therein for mating with the hexagonal outer surface of the locking nut 18. In use, the wrench 520 is inserted over the fastener inserter tool 500 until the locking nut 18 is received within the socket 528. The handle 524 of the wrench 520 is then rotated to rotate the locking nut 18, thereby threading the locking nut 18 onto the staple body 12. As a result, tether 50 is engaged between the washer 16 and the staple body 12 such that it is maintained in a substantially fixed position. Additional locking assemblies can be applied to additional spinal anchoring devices to lock the tether 50 thereto. Tension can be applied to the tether 50 between each anchoring device prior to or while applying the locking assemblies to achieve a desired result. FIG. 18 illustrates tether 50 extending between two spinal anchoring devices 10, 10'.

While FIG. 18 illustrates a single tether 50 positioned on one side of the spine, multiple tethers can be used depending on the deformities to be corrected. As previously indicated, the tether is preferably positioned on the concave side of a deformed spinal curve, thereby halting growth on the convex side of the deformity. Thus, where the spine is curved at multiple locations, multiple tethers can be used. For example, three spinal anchoring devices can be placed in the sagittal plane on the concave side of the curve in the spinal column at a first level, and three additional spinal anchoring devices can be placed on the opposed side of the spinal column at a second level such that the three additional spinal anchoring devices are placed on the concave side of a second curvature formed in the spinal column. A tether can thus be positioned to span between the spinal anchoring devices at the first level, and a second tether can be positioned to span between the spinal anchoring devices at the second level on the opposite side of the spine. Tension can then be applied to each tether and the tethers can be locked relative to each spinal anchoring device as previously discussed. The tension between each vertebra can vary depending on the desired correction, which can be accomplished intraoperatively by tensioning the tethers to achieve the correction immediately, and/or by allowing normal growth of the spine to achieve correction by asymmetrically restricting growth using the tether. Once correction has been achieved, the tethers can optionally be cut to release the tension at one or more levels. In one embodiment, the tethers can be cut in a minimally invasive procedure. Cutting the tethers is particularly advantageous to prevent over-correction.

As noted above, the position of each fixation element along the patient's spinal column will vary depending on the spinal deformity being corrected. In other exemplary embodiments, to achieve correction of a scoliotic deformity in the frontal plane, both tethers can be placed on the convex side of the curve, with one posterior tether and one anterior tether. The tethers can be mated to the vertebrae by several spinal anchoring devices that are implanted adjacent to one another within each of several adjacent vertebrae. Tension can then be applied to both the anterior and posterior tethers by selectively fastening the anchoring devices to lock the tethers therein. To correct only the frontal plane deformity, equal tension is preferably applied to both tethers, and the degree of tension dictates how much correction is achieved intraoperatively and how much is left to take place during asymmetric growth restriction.

To achieve correction of a saggittal plane deformity in addition to correction of a scoliotic deformity, the anterior and posterior tethers are preferably tensioned differently. To increase lordosis, the posterior tether is tightened more than the anterior tether. To increase kyphosis, the anterior tether a is tightened more than the posterior tether. Similar to correcting the scoliotic deformity, the degree of tension dictates how much correction is achieved intraoperatively and how much is left to take place during asymmetric growth restriction.

In certain exemplary applications, the implants and instruments described herein are designed to be used in a minimally invasive surgical procedure; thus the dimensions are such that they can be inserted through a portal with an inner diameter of approximately 5 to 30 mm, more preferably 15-20 mm. This is particularly important when the implants are being used to correct a cosmetic deformity, where lengthy incisions would negate the positive cosmetic effect of the correction.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for correcting spinal deformities, comprising:
    implanting a staple in bone;
    inserting a fastening element through the staple and into the bone;
    positioning a substantially flat elongate flexible tether between opposed arms formed on the staple; and
    applying a locking element to the staple to engage the tether, the locking element extending around and engaging an outer surface of the opposed arms formed on the staple and extending circumferentially around a head of the fastening element.

2. The method of claim 1, wherein implanting the staple in bone comprises impacting the staple into bone, and inserting the fastening element through the staple and into the bone comprises inserting the fastening element into a bone hole to secure the staple to bone.

3. The method of claim 1, wherein inserting the fastening element through the staple comprises inserting the fastening element into the bone hole to drive the staple into bone.

4. The method of claim 1, wherein the opposed arms define a pathway therebetween for receiving the tether.

5. The method of claim 4, wherein applying a locking element to the staple comprises positioning a washer around the opposed arms of the staple such that the tether is positioned between the washer and the staple, and mating the locking element to the opposed arms.

6. The method of claim 1, wherein the locking element includes a washer having opposed arms extending therefrom.

7. The method of claim 1, further comprising deforming the flexible tether over a tether-engaging feature in the pathway defined by the opposed arms.

8. A method for correcting spinal deformities, comprising:
    implanting a staple in bone, the staple having a fastening element extending therethrough to fix the staple to bone;
    positioning a tether through a non-linear pathway formed in the staple such that the tether is deformed over a tether-engaging feature in the non-linear pathway; and;
    applying a locking assembly to the staple and around the tether engaging feature to engage the tether and substantially prevent movement relative to the staple.

9. The method of claim 8, wherein the staple is adapted to penetrate bone.

10. The method of claim 9, wherein the staple is impacted into bone prior to inserting the fastening element therethrough.

11. The method of claim 9, wherein the fastening element is used to drive the staple into bone.

12. The method of claim 9, wherein applying the locking assembly comprises coupling a washer to the staple such that the tether is disposed between the washer and the staple, and applying a locking nut to the staple to lock the washer and tether relative to the staple.

13. The method of claim 12, wherein the staple includes opposed arms formed thereon that define the pathway therebetween.

14. A method for correcting spinal deformities, comprising:
    impacting at least one bone-penetrating member formed on an inferior surface of a staple body into a vertebra;
    inserting a fastening element through the staple body and into the vertebrae to attach the staple to the vertebra such that a head of the fastening element is positioned between opposed arms formed on the staple;
    positioning a tether on a superior surface of the staple between the opposed arms such that the tether extends over the head of the fastening element; and
    applying a locking mechanism to the staple such that the locking mechanism and the staple engage the tether therebetween to maintain the tether in a substantially fixed position relative to the staple, the locking mechanism extending around and engaging an outer surface of the opposed arms formed on the staple.

15. The method of claim 14, wherein the staple body includes a pathway for seating the tether, and wherein the head of the fastening element alters the pathway.

16. The method of claim 15, further comprising deforming the tether over the head of the fastening element within the pathway.

17. The method of claim 14, wherein the tether is substantially planar.

18. The method of claim 14, wherein the tether is maintained between the locking mechanism and the staple body in a non-linear pathway.

19. The method of claim 14, wherein the tether extends along a pathway between the opposed arms.

20. The method of claim 19, wherein the locking mechanism is adapted to mate to threads formed on the opposed arms.

21. The method of claim 20, wherein the locking mechanism includes a washer and a locking nut adapted to engage the opposed arms and lock the tether between the washer and the staple body.

22. The method of claim 21, wherein the washer includes an outer portion adapted to be positioned around the opposed arms, and a strut extending between opposed sides of the outer portion and adapted to be positioned between the opposed arms.

23. The method of claim 14, wherein the locking mechanism includes a washer having opposed arms extending therefrom.

\* \* \* \* \*

UNITED STATES PATENT AND TRADEMARK OFFICE
CERTIFICATE OF CORRECTION

| | | |
|---|---|---|
| PATENT NO. | : 7,909,826 B2 | Page 1 of 1 |
| APPLICATION NO. | : 10/907232 | |
| DATED | : March 22, 2011 | |
| INVENTOR(S) | : Serhan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 618 days.

Signed and Sealed this
Fifth Day of July, 2011

David J. Kappos
*Director of the United States Patent and Trademark Office*